United States Patent [19]

Lown et al.

[11] Patent Number: 5,616,606
[45] Date of Patent: Apr. 1, 1997

[54] OLIGOPEPTIDE ANTIRETROVIRAL AGENTS

[75] Inventors: J. William Lown, Edmonton; Ronald G. Micetich, Sherwood Park, both of Canada

[73] Assignees: Synphar Laboratories, Inc., Alberta, Canada; Taiho Pharmaceutical Co., Ltd., Tokyo, Japan

[21] Appl. No.: 510,333

[22] Filed: Aug. 2, 1995

Related U.S. Application Data

[63] Continuation of Ser. No. 102,715, Aug. 6, 1993, abandoned.
[51] Int. Cl.$^6$ .................... A61K 37/00; C07C 103/52; C07K 7/06
[52] U.S. Cl. .................. 514/422; 548/518; 514/18; 514/19; 530/331; 530/329; 530/330
[58] Field of Search ..................... 514/422; 548/518

[56] References Cited

U.S. PATENT DOCUMENTS 4,912,199  3/1990  Lown et al. ........................ 530/331

FOREIGN PATENT DOCUMENTS

WO92/13838  8/1992  WIPO .

OTHER PUBLICATIONS

J. Org. Chem. 1991, vol. 56, No. 2, "Sequence–Selective DNA Binding by Linked Bis–N–methylpyrrole Dipeptides: An Analysis by MPE Footprinting and Force Field Calculation", Ekambareswara et al, pp. 786–797.

J. Med. Chem. 1989, vol. 32, No. 10, "Novel Linked Antiviral and Antitumor Agents Related to Netropsin and Distamycin: Synthesis and Biological Evaluation", Lown et al, pp. 2368–2375.

*Primary Examiner*—Robert T. Bond
*Attorney, Agent, or Firm*—Nikaido, Marmelstein, Murray & Oram LLP

[57] ABSTRACT

Oligopeptide antiretroviral agents are represented by formula (I), wherein A is a moiety bearing a positive charge and of a size which avoids steric inhibition of binding of said compound to nucleic acid sequences associated with the cellular activity of retroviruses; $R_1$ is a moiety derived from a dicarboxylic acid; Hew is a five-membered heterocyclic moiety; y and z are independently 0, 1, 2 or 3; and x is 0 or 1. These compounds exhibit antiretroviral activity, especially against Human Immunodeficiency Virus (HIV).

$$A-(NHCO)_x-\underset{R_2}{Het}-(NHCO-\underset{R_3}{Het})_y-NR-R_1- \quad (I)$$

$$-NH-(\underset{R_4}{Het}-CONH)_z-\underset{R_5}{Het}(CONH)_x-A$$

31 Claims, 6 Drawing Sheets

OLIGOPEPTIDE ANTIRETROVIRAL AGENTS

CROSS-REFERENCE TO RELATED APPLICATION

This application is a continuation of application Ser. No. 08/102,715 filed Aug. 6, 1993, abandoned which is a continuation-in-part of International Application PCT/CA92/00051 filed Feb. 5, 1992.

FIELD OF THE INVENTION

This invention relates to oligopeptides which are particularly useful as antiretroviral agents.

BACKGROUND OF THE INVENTION

Various oligopeptide derivatives have demonstrated various medicinal uses, such as enzyme inhibitors as disclosed in U.S. Pat. No. 4,483,850. It is also known that various oligopeptides have anti-tumor activity as disclosed in U.S. Pat. Nos. 4,216,208 and 4,314,999. Antibiotic activity of oligopeptides is disclosed in U.S. Pat. No. 4,454,065. Naturally occurring oligopeptides, netropsin and distamycin, have been discovered as having antiviral and anti-tumor activity. The chemical formulas for netropsin and distamycin are as follows:

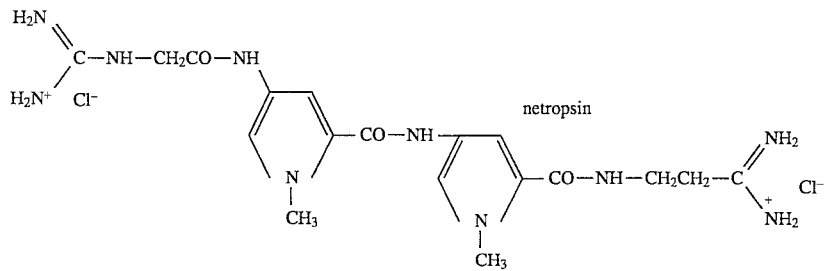

Compound 1

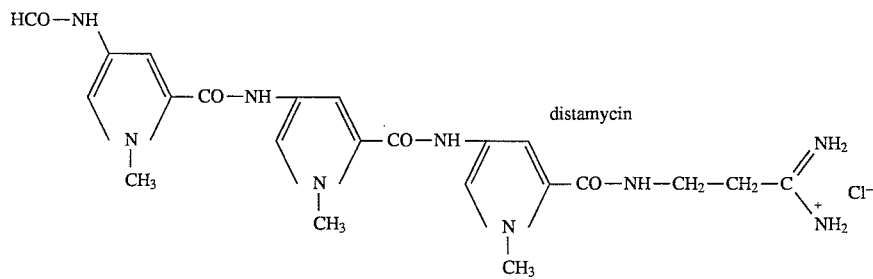

Compound 2

These oligopeptides are disclosed in Julia, M., Préau-Joseph, N., C. R. Hebd-Seances, *Acad. Sci.* 1963, 257. 1115 and Arcamone, F.; Orezzi, P. G.; Barbier, W.; Nicolella, V.; Penco, S.; *Gazz. Chim. Ital.,* 1967, 97, 1097.

Netropsin and distamycin contain pyrrole moieties connected by peptide bonds and with side chains, at least one of which is positively charged; i.e., an amidine group, or a group of the guanidyl type.

Only distamycin has been used as a therapeutic agent as commercialized and sold under the trade mark STALLIMY-CIN HYDROCHLORIDE in the form of a 1% cream, ointment or paste. This composition has been used in the treatments of infections produced by herpes simplex, herpes zoster and vaccinia viruses. Topical application of distamycin has been limited due to its high cytotoxicity and a low therapeutic index which in the instance of treating the herpes virus is about 3.

U.S. Pat. No. 4,912,199 discloses oligopeptides containing pyrrole moieties which demonstrated significantly enhanced antiviral and anticancer activities as compared to the oligopeptides of the prior art.

According to this invention oligopeptides have been developed which have significantly enhanced antiretroviral activity compared to prior types of oligopeptides.

SUMMARY OF THE INVENTION

According to an aspect of the invention, a compound represented by the formula I:

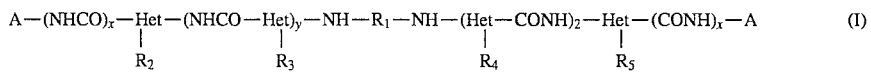

wherein A is a moiety bearing a positive charge and of a size which does not inhibit binding of said compound to nucleic acid sequences associated with the cellular action of retroviruses; $R_1$ is a moiety derived from a dicarboxylic acid or a residue of carbonic acid; Hew is a five-membered heterocyclic moiety; y and z are independently 0, 1, 2 or 3, x is 0 or 1, and pharmaceutically acceptable salts thereof, exhibit antiretroviral activity, especially against Human Immunodeficiency Virus and Hepititus B Virus.

A process for preparing such compounds comprises reacting a compound of the formula (II):

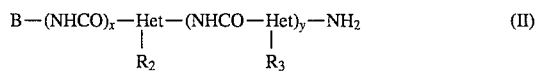

wherein x and y are as defined above; and B is the same as A or is a group with a nitrile, halogen or sulfide substituent; with a dicarboxylic acid of the formula (III):

wherein $R_1$ is as defined above and X is halogen, imidazolide or other reactive moiety and converting B to A to form said moiety bearing a positive charge.

DETAILED DESCRIPTION OF THE PREFERRED EMBODIMENTS

Figure 1:
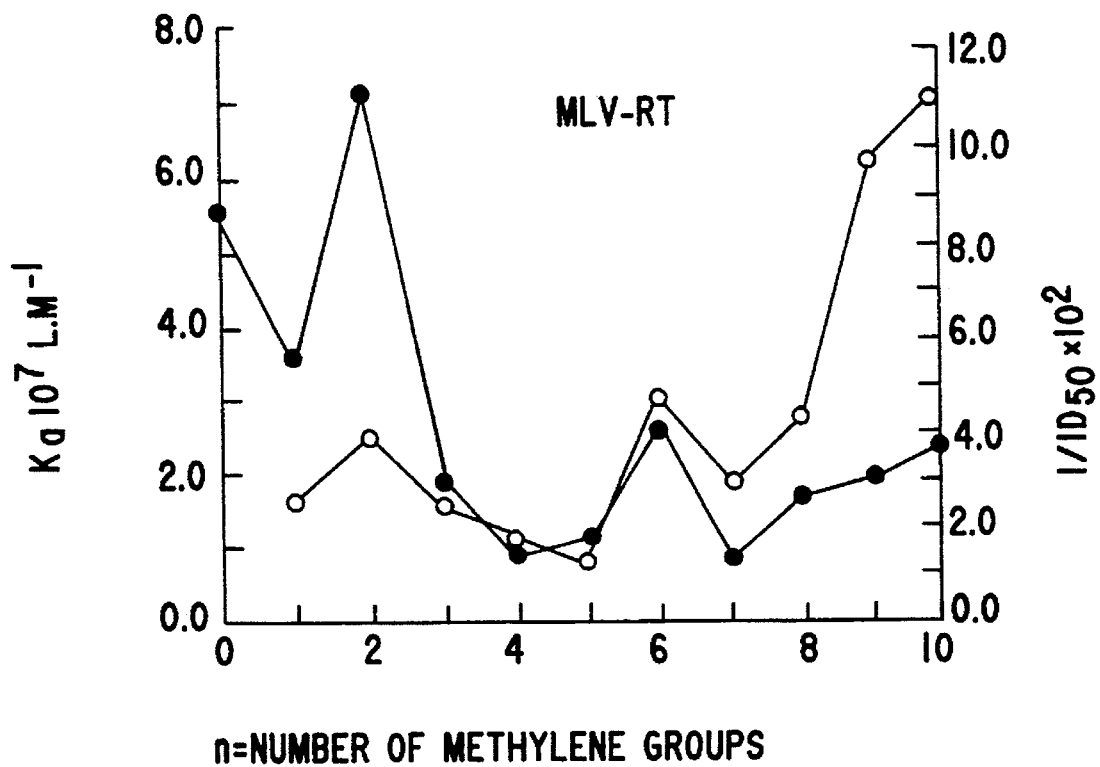
FIG. 1 is a graph showing a correlation between DNA binding constants of linked oligopeptides ($K_a$, –) and observed inhibitory properties expressed in reciprocal $ID_{50}$ values against Moloney Leukemia Virus reverse transcriptase (MIV-RT).
Figure 2:
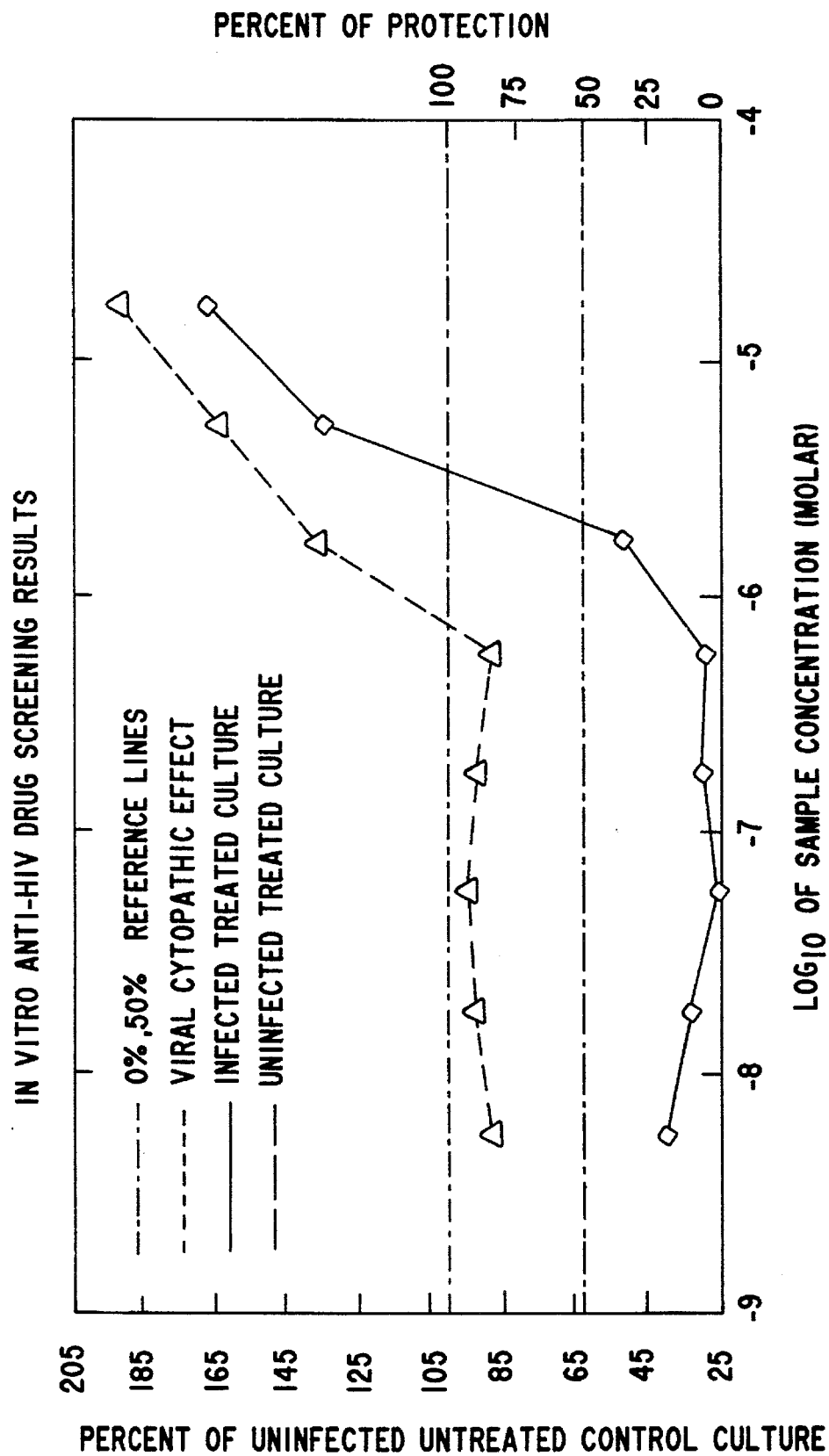
FIGS. 2–6 are graphs showing anti-HIV activity of several compounds of the present invention.
Figure 3:
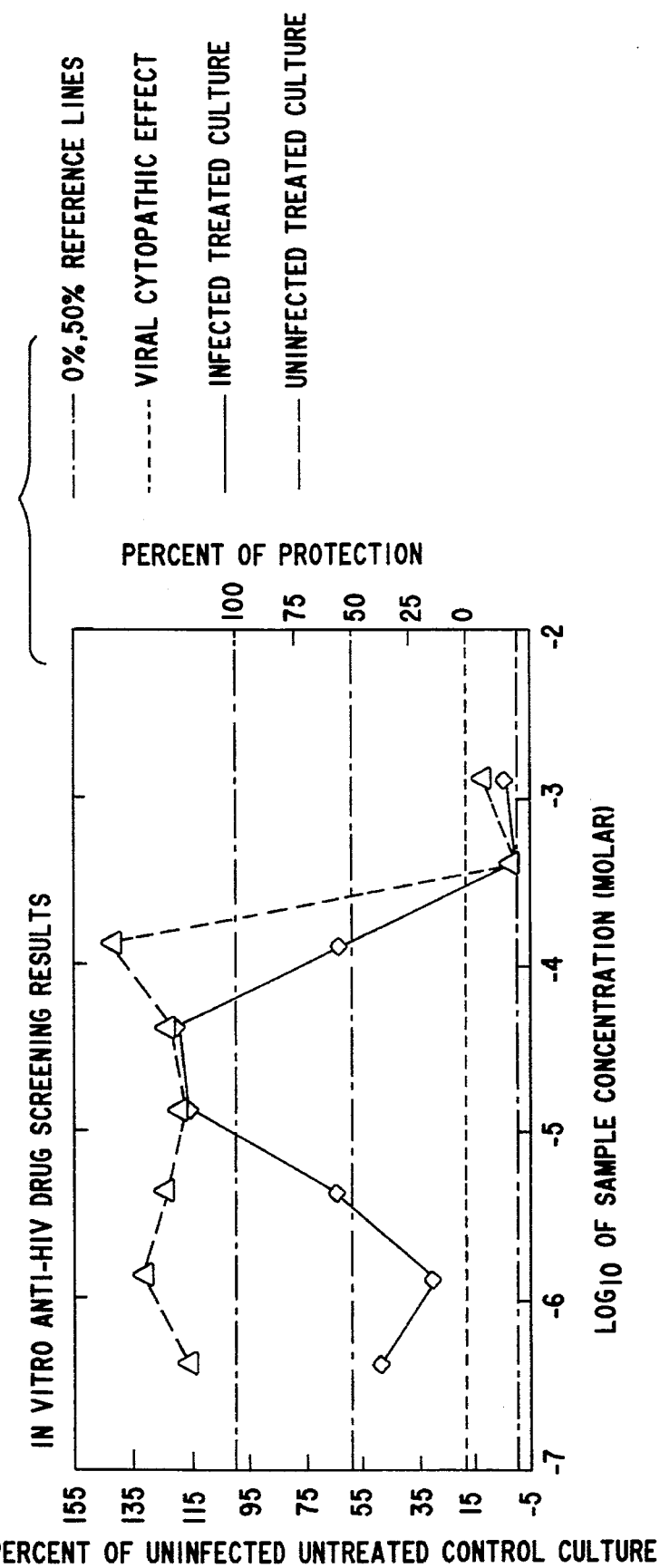
Figure 4:
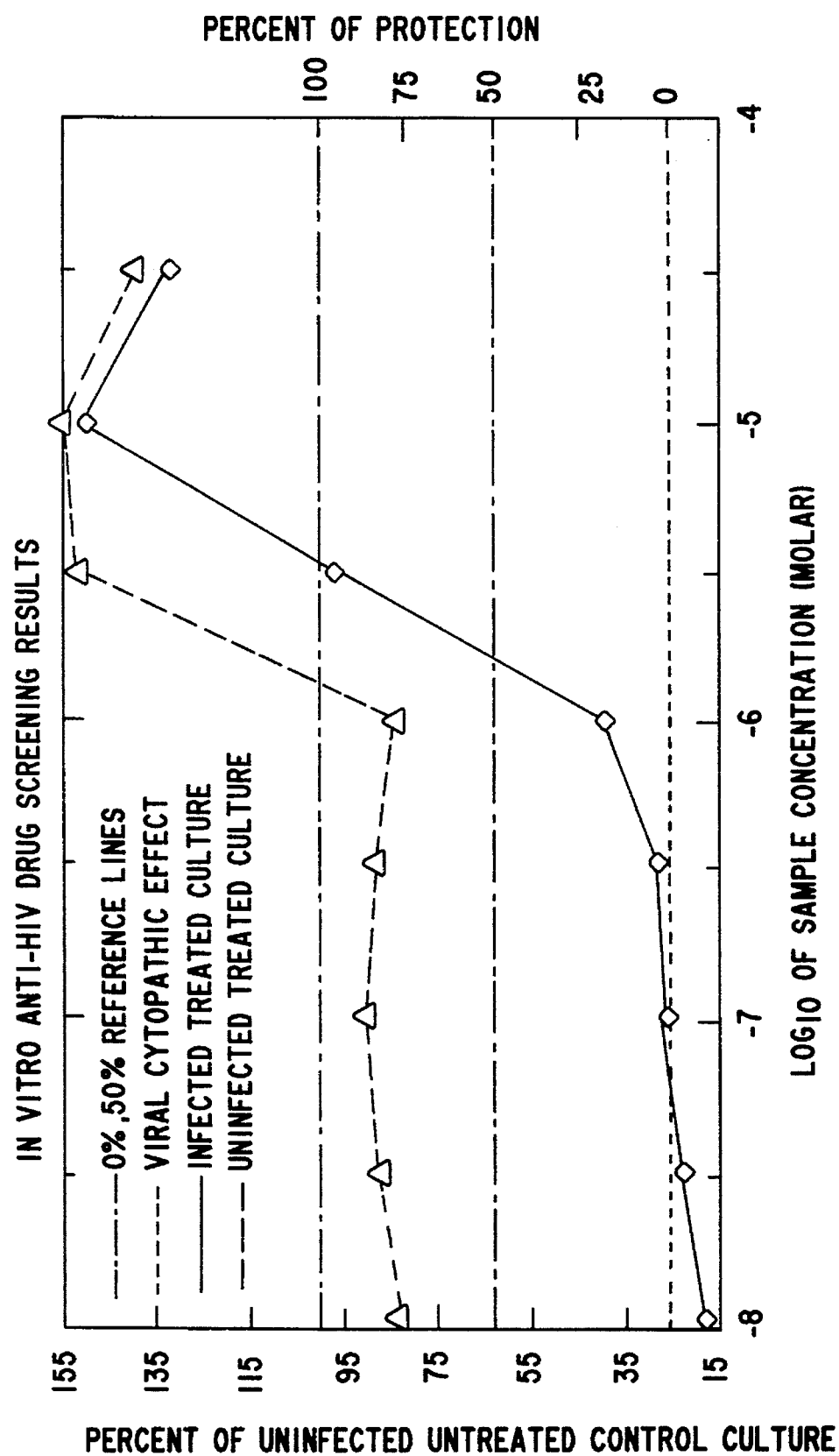
Figure 5:
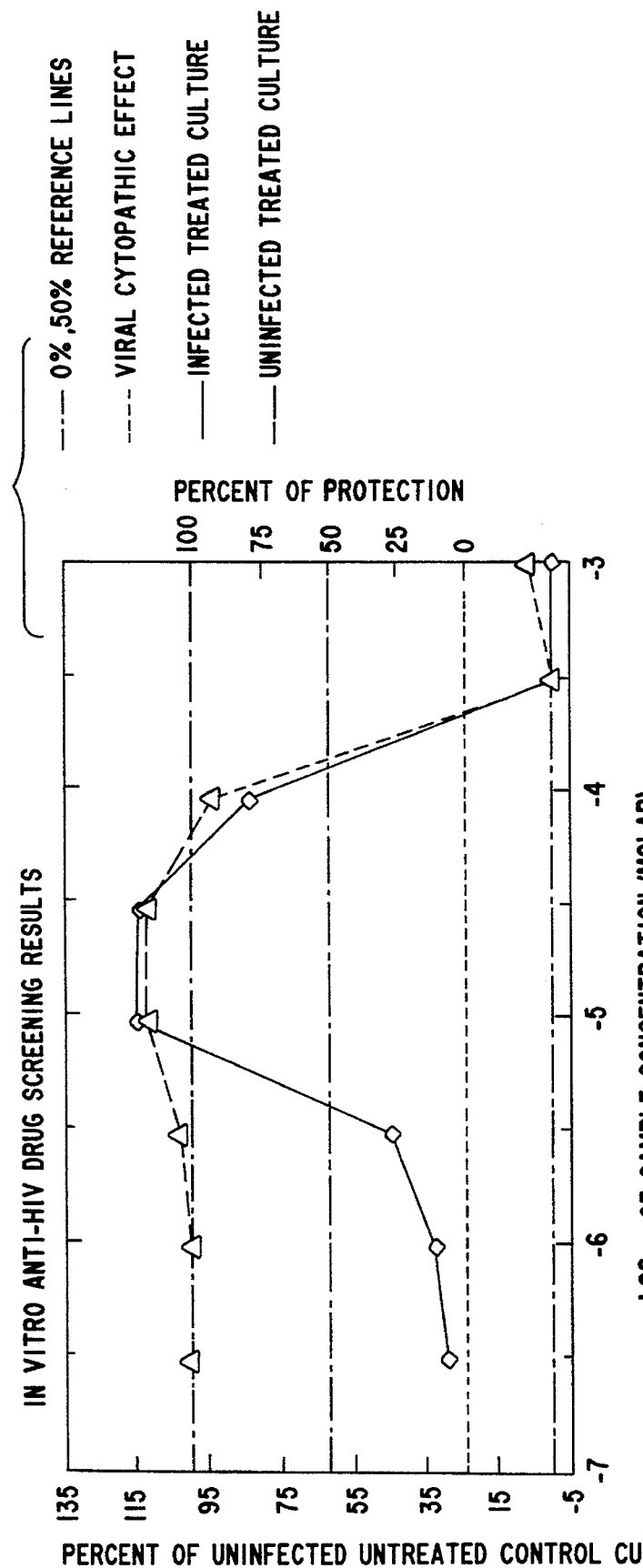
Figure 6:
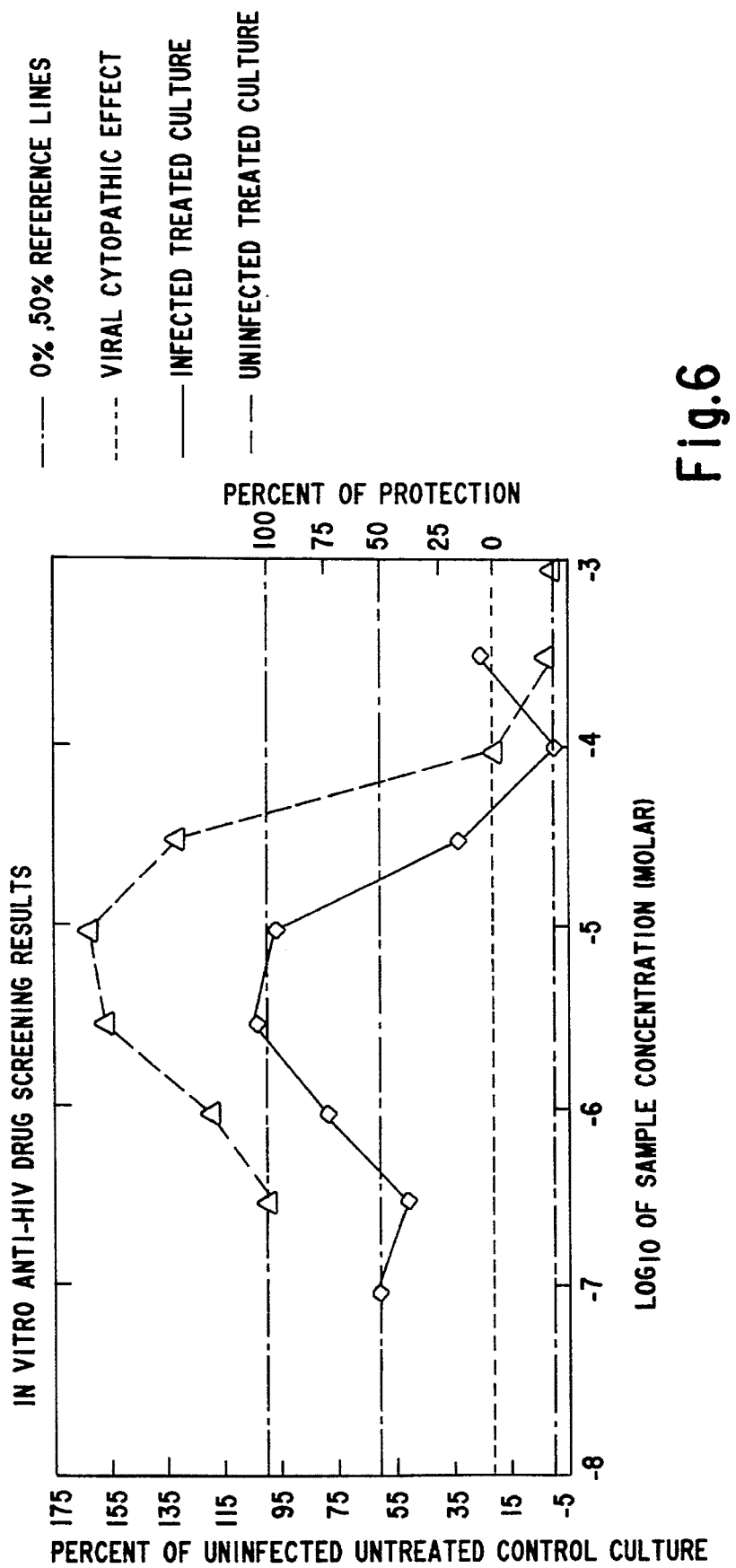

Compounds according to this invention demonstrate significant antiretroviral activity. Although the actual biological mechanism of these compounds which cause antiretroviral activity is not fully understood, it is thought that the activity may be due to the compounds of this invention binding with nucleic acid sequence(s) associated with the cellular action of retroviruses to inactivate such nucleic acids which code for the retroviral activity. It has also been observed that the linked oligopeptides of the present invention are potent inhibitors of Moloney Leukemia Virus (MIV) reverse transcriptase, a potential indicator of anti-HIV activity. See FIG. 1.

The compounds of this invention have heterocyclic moieties, which may be the same or different, linked by a dicarboxylic acid derivative. Such linked heterocyclic moieties of this invention have significant unexpected activity compared to unlinked pyrrole moieties such as the naturally occurring netropsin and distamycin.

The compounds according to this invention are represented by the following formula:

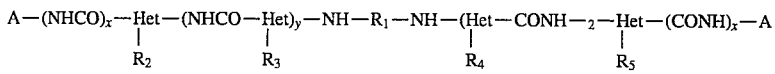

wherein A is a moiety bearing a positive charge and of a size which does not inhibit binding of said compounds to deoxyribonucleic acid sequences associated with the cellular action of retroviruses: $R_1$ is a moiety derived from a dicarboxylic acid; Hew is a five-membered heterocyclic moiety: $R_2$, $R_3$, $R_4$ and $R_5$ may be attached to a ring carbon atom or hetero ring atom and are independently selected from $C_1$–$C_6$ alkyl and $CH_2$—O—$R_6$, where $R_6$ is a $C_1$–$C_6$ alkyl; y and z are independently 0, 1, 2 or 3; x is 0 or 1; and pharmaceutically acceptable salts thereof.

The positively charged moiety at each extremity of the compound and identified as group A is preferably selected from the group of derivatives consisting of an amidine, a guanidine, secondary ammonium salts, sulfonium salts and phosphonium salts.

The selected amidine may have one or both nitrogen atoms of the amidine as a member of a five-membered cyclic structure. More particularly, the amidine derivative is represented by the formula:

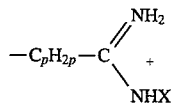

where p equals 0 to 5 and X is —H, —OH, —$NH_2$, —$CH_3$, —$C_2H_5$, —$C_3H_7$.

The selected quanidine for substituent A may be represented by the formula:

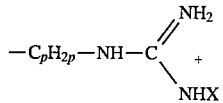

where p equals 0 to 5 and X equals —H, —OH, —$NH_2$, —$CH_3$, —$C_2H_5$, —$C_3H_7$.

When A is selected to be quaternary, tertiary or secondary ammonium salt, it may be represented by the formula:

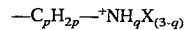

where p equals 1 to 5 and q equals 0 to 3 and X is an alkyl or alkenyl group of 1 to 3 carbon atoms.

When A is selected as a sulfonium salt, it may be represented by the formula:

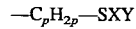

where p equals 0 to 5 and X and Y are alkyl or alkenyl groups of 1 to 3 carbon atoms.

In the heterocyclic moieties, Hew may be the same in each moiety or may be different. Preferably, the Hew group is selected from the group consisting of a pyrrole, an imidazole, a triazole, a pyrazole, a thiazole, a thiophene, a furan, an oxazole and derivatives thereof.

Preferred ring carbon atom substituents are alkyl groups, and especially methyl groups, on the Hew moiety, especially on thiazole rings.

Preferred Hew substituents are N-alkyl pyrrole having 1 to 6 carbon atoms in the alkyl group; N-alkyl imidazole having 1 to 6 carbon atoms in the alkyl group; alkyl pyrazole having 1 to 6 carbon atoms in the alkyl group; and alkyl triazole having 1 to 6 carbon atoms in the alkyl group. Preferably the N-alkyl pyrrole has 1 to 4 carbon atoms in the alkyl group, and especially in N-methyl pyrrole. Also preferred Hew substituents are N-linked alkoxymethyl groups. The choice of Hew substituents will depend on their cellular uptake ability.

$R_2$, $R_3$, $R_4$ and $R_5$ are linked to the N or C atom of the Hew moiety and are independently $C_1$–$C_6$ alkyl or —$CH_2$—O—$R_6$ where $R_6$ is $C_1$–$C_6$ alkyl. It has been found that the longer the alkyl group in either structure is, the better the cellular uptake of the compound. The choice of substituent will depend on solubility properties; solubility in pharmacologically acceptable solvents, such as water or DMSO, has been found to be higher with the methoxy substituents.

The linking group $R_1$ is a derivative from carboxylic acid. $R_1$ is represented generally by the formula:

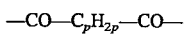

where p equals any number from 1 to 22. Alternatively, $R_1$ may be a residue of carbonic acid, namely

or $R_1$ may be a residue of an aromatic dicarboxylic acid. The —CO— groups of the aromatic dicarboxylic acid residues may be in the ortho, meta or para positions on the ring. The aromatic residues may be 5 to 6 C membered rings. The aromatic dicarboxylic acid may also be a six membered heterocylic ring containing a nitrogen atom.

Other alternative structures for the linking group may be a residue of an unsaturated aliphatic dicarboxylic acid of the formula:

$$-CO-C_qH_{(2q-2)}-CO-$$

where q equals any number from 2 to 22.

$R_1$ may also be a residue of cycloalkane dicarboxylic acids of the formula:

$$-CO-C_rH_{(2r-2)}-CO-$$

where r equals any number from 3 to 7 and optionally may be fused to one or more three to seven C membered rings, preferably fused to one or two three to seven C membered rings.

$R_1$ may also be a residue of cycloalkane dicarboxylic acids of the formula:

$$-CO-C_sH_{(2s-4)}-CO-$$

where s equals any number from 3 to 7.

In a preferred compound of the present invention, A is a moiety selected from the group consisting of an amidine, a guanidine, secondary ammonium salts, tertiary ammonium salts, quaternary ammonium salts, sulfonium salts and phosphonium salts.

In another preferred compound of the present invention, $R_2$, $R_3$, $R_4$ and $R_5$ are each a $C_1$–$C_6$ alkyl or $R_2$, $R_3$, $R_4$ and $R_5$ are the same are a $C_1$–$C_6$ alkyl group or $R_2$, $R_3$, $R_4$ and $R_5$ are each a methoxymethyl.

In another preferred compound of the present invention, $R_1$ is

or $R_1$ is a residue of a dicarboxylic acid of the formula $-CO-C_pH_{2p}-CO-$ where p equals 1 to 22. $R_1$ may also be preferably a residue of a dicarboxylic acid selected from the group consisting of: a residue of an unsaturated aliphatic dicarboxylic acid of the formula $-CO-C_q-H_{2q-2}-CO-$ where q equals 2; a residue of an aromatic dicarboxylic acid; and a residue of a cycloalkane dicarboxylic acid of the formula $-CO-C_r-H_{2r-2}-CO-$ where r equals 3 to 6.

In yet another preferred compound, $R_1$ is

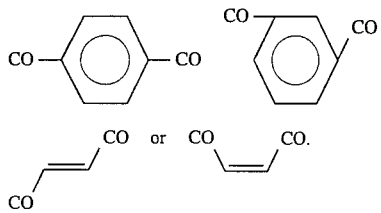

Preferably, $R_1$ is a dicarboxylic acid residue of cyclopropane, a dicarboxylic acid residue of cyclopentane, or a dicarboxylic acid residue of cyclohexane.

The following are representative examples of the preferred compounds of the present invention.

N, N'-di[1-methyl-2-[1-methyl-2-carboximido(3-propionamidine)-4-pyrrole]-4-pyrrolyl]terephthalamide dihydrochloride.

N, N'-di[1-methyl-2-[1-methyl-2-carboximido(3-propionamidine)-4-pyrrole]-4-pyrrolyl]isophthalamide dihydrochloride.

N, N'-di[1-methyl-2-[1-methyl-2-carboximido(3-propionamidine)-4-pyrrole]-4-pyrrolyl]fumaramide dihydrochloride.

N, N'-di[1-methyl-2-[1-methyl-2-carboximido(3-propionamidine)-4-pyrrole]-4-pyrrolyl]maleamide dihydrochloride.

N, N'-di[1-methyl-2-[1-methyl-2-carboximido(3-propionamidine)-4-pyrrole]-4-pyrrolyl] trans 1,2-cyclobutanamide dihydrochloride.

N, N'-di[1-methyl-2-[1-methyl-2-carboximido(3-propionamidine)-4-pyrrole]-4-pyrrolyl] trans 1,2-cyclobutanamide dihydrochloride.

The compound:

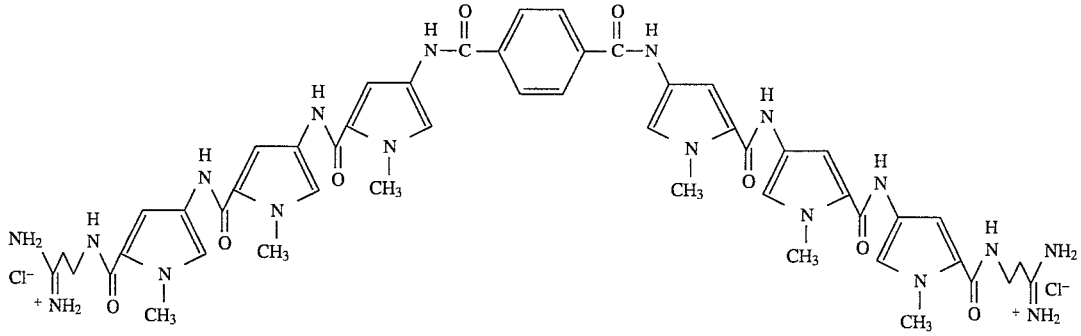

The compound:

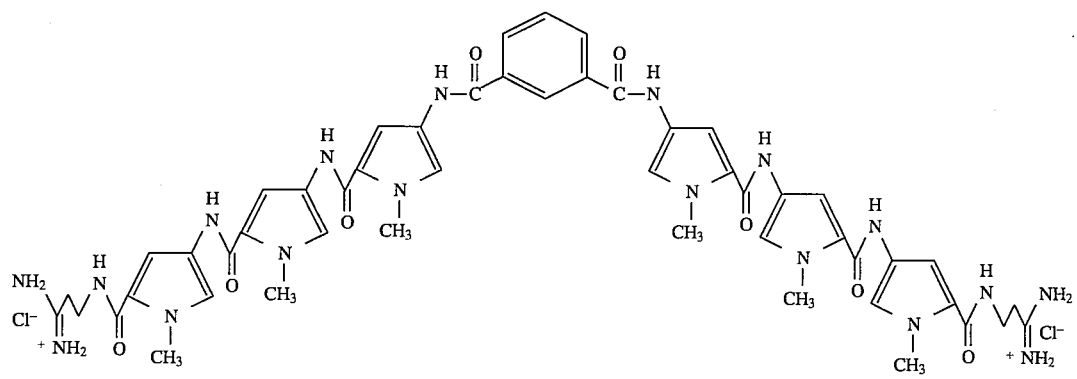
The compound:
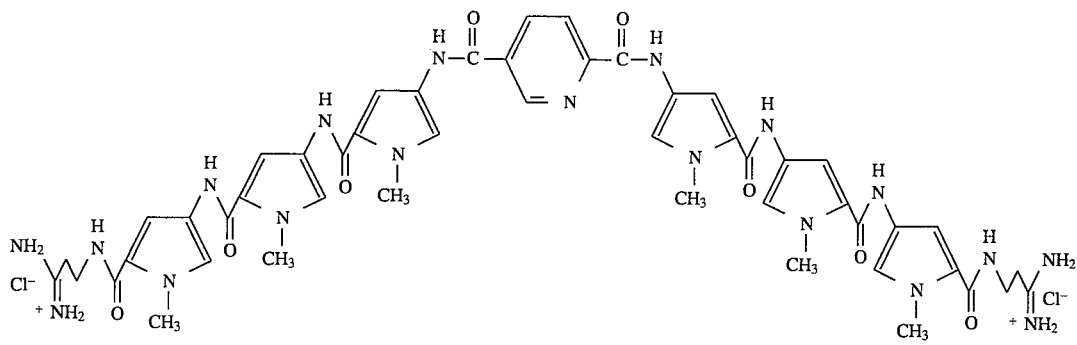
The compound:
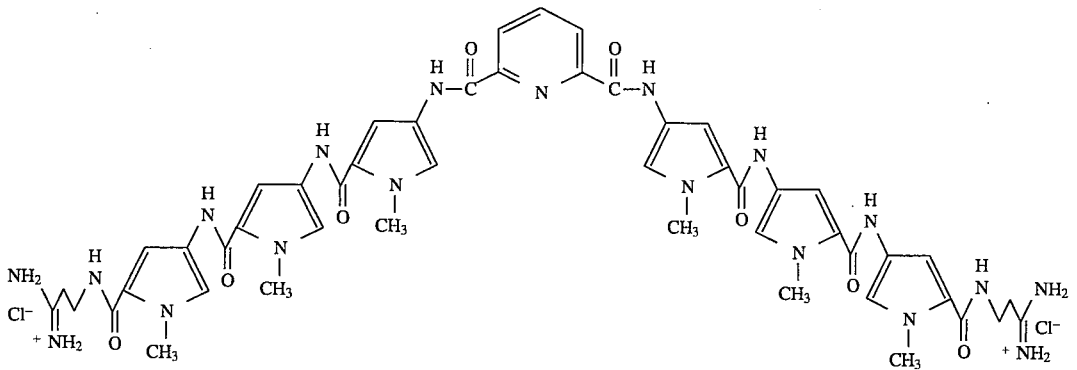
The compound:

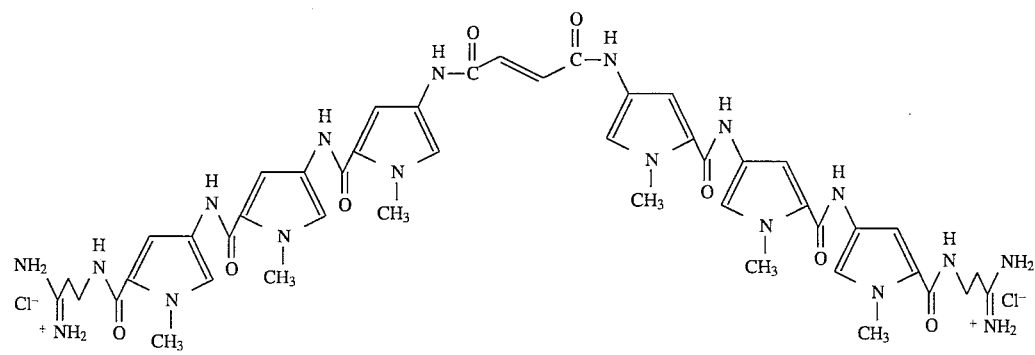

15

In cases where $R_1$ is a dicarboxylic acid derivative of an aliphatic hydrocarbon, the linker is referred to as flexible. Rigid linkers refer to cases in which $R_1$ is carbonic acid or residues of aromatic, unsaturated aliphatic, cycloalkane and cycloalkene dicarboxylic acids. Most preferred are those compounds in which $R_1$ is a rigid linker. Examples of the flexible linked and rigid linked oligopeptides are set forth below.

FLEXIBLE LINKED OLIGOPEPTIDES

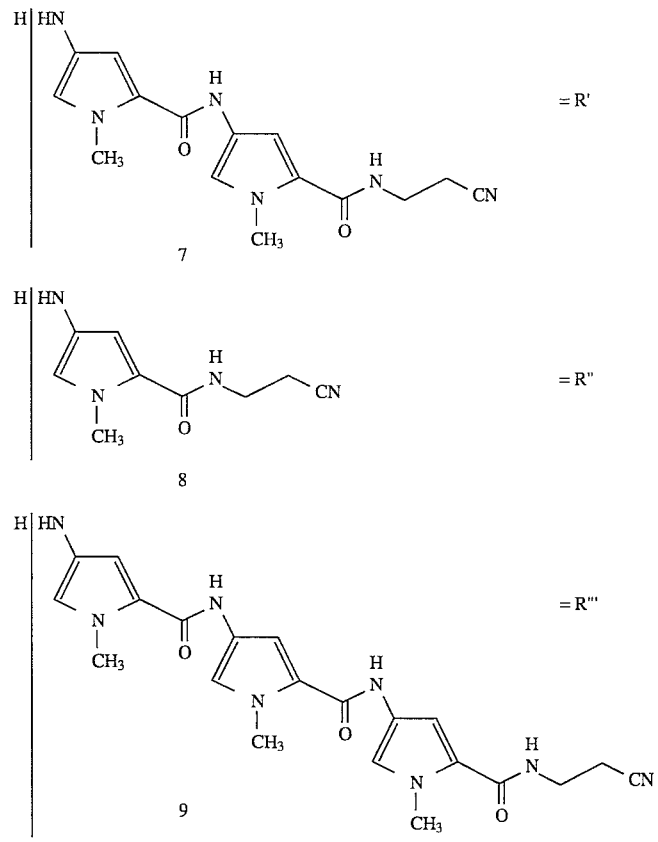

R'—CO—(CH$_2$)$_n$—COR'
R"—COCH$_2$CH$_2$COR"
R'"—COCH$_2$CH$_2$COR'"

-continued
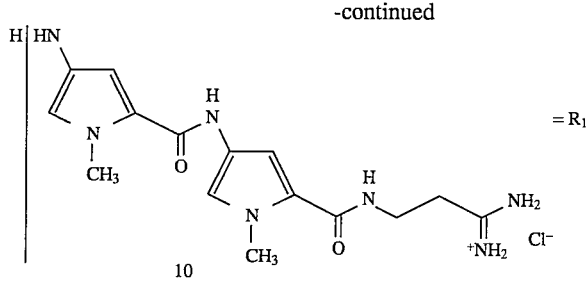
= R₁
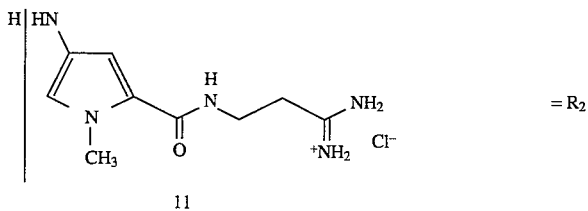
= R₂
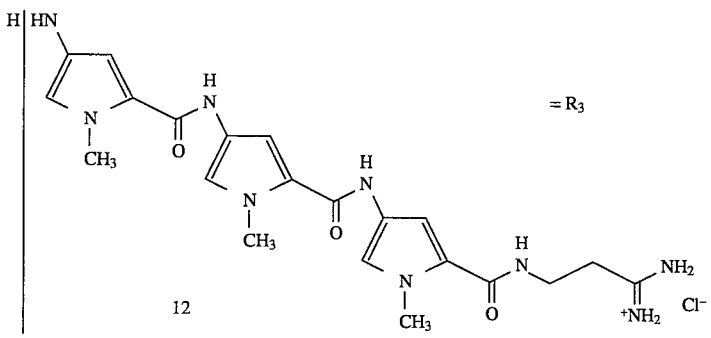
= R₃
R₁—CO—(CH₂)ₙ—COR₁
R₂—CO—CH₂CH₂—CO—R₂
R₃—CO—CH₂CH₂—CO—R₃
3  R₁—CO—R₁
4  R₁—COCH₂CO—R₁
5  R₁—CO(CH₂)₂CO—R₁
6  R₁—CO(CH₂)₃CO—R₁
7  R₁—CO(CH₂)₄CO—R₁
8  R₁—CO(CH₂)₅CO—R₁
9  R₁—CO(CH₂)₆CO—R₁
10 R₁—CO(CH₂)₇CO—R₁
11 R₁—CO(CH₂)₈CO—R₁
12 R₁—CO(CH₂)₉CO—R₁
13 R₁—CO(CH₂)₁₀CO—R₁
14 R₂—CO(CH₂)₂CO—R₂
15 R₃—CO(CH₂)₂CO—R₃
16 R₃—CO(CH₂)₆CO—R₃
17 R₃—CO(CH₂)₈CO—R₃
18 R₃—CO(CH₂)₂₂CO—R₃
Rigid Linked Oligopeptides
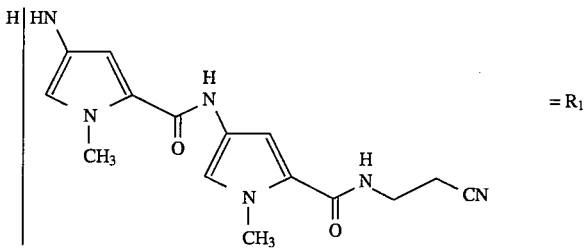
= R₁

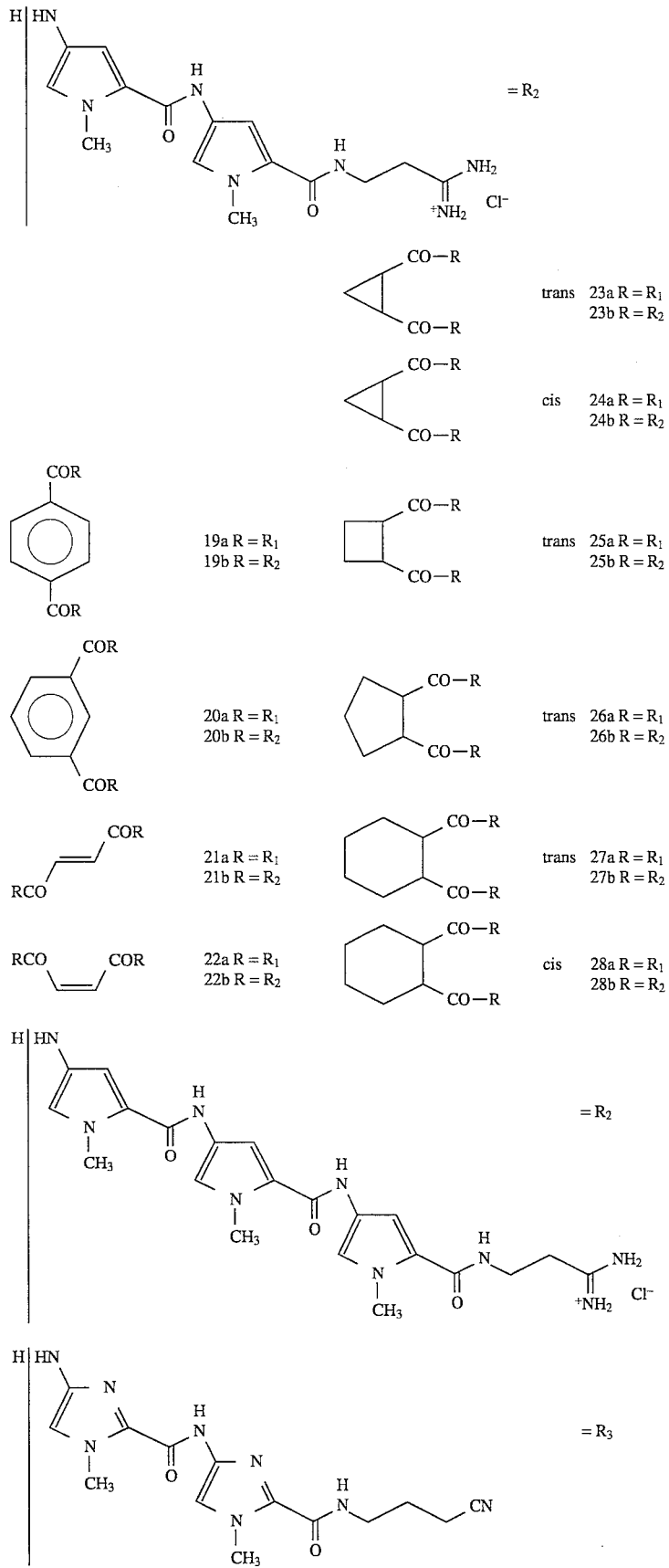

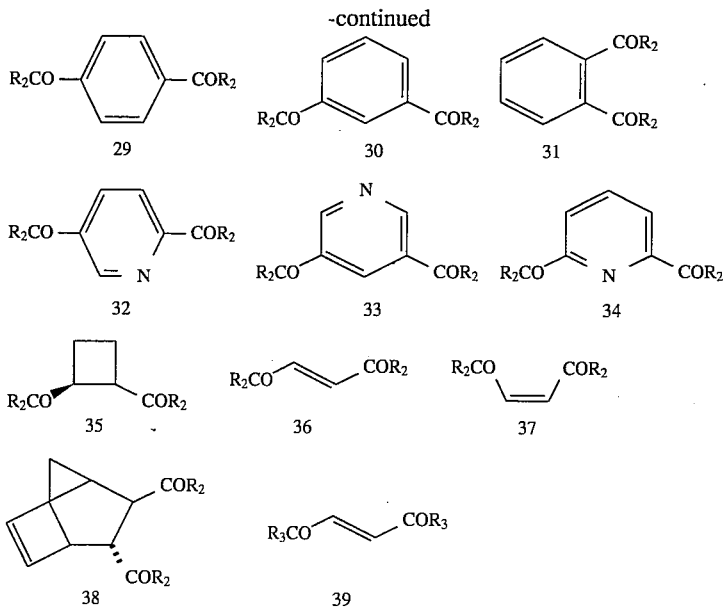

Other preferred compounds include compounds of formula I wherein Hew is pyrrole and x is 1; A is:

$$-CH_2CH_2-C\begin{array}{c}NH_2\\ \diagup\\ \diagdown\\ ^+NH_2\end{array}$$

and $R_1$ is a rigid linker (as defined above).

The heterocyclic moiety of the compounds of this invention may be linked in accordance with various processes by use of the dicarboxylic acid derivatives. In accordance with one aspect of this invention, the process for providing such linkage comprises reacting a compound of the formula:

$$B-(NHCO)_x-\underset{R_2}{Het}-(NHCO-\underset{R_3}{Het})_y-NH_2$$

wherein x and y are as defined above; and B is the same as A or is a group with a nitrile, halogen or sulfide substituent; with a dicarboxylic acid of the formula:

$$X-R_1-X$$

wherein $R_1$ is as defined above and X is halogen, imidazolide or other reactive moiety and converting B to A to form said moiety bearing a positive charge.

In the reactants, B may be generally represented by the formula:

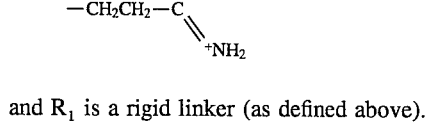

where Z is CN—, hal or XS; hal is a halogen ion, X is an alkyl or alkenyl group having 1 to 3 carbon atoms, and p equals 0 to 5.

It is to be appreciated that B may also be identical to A in providing a charge group, for example, a guanidinium end group. In that instance, B has the general formula:

$$\begin{array}{c}H_2N\\ \diagdown\\ C-(NH)_s-C_pH_{2p}-\\ \diagup\\ XNH^+\end{array}$$

wherein X is an alkyl having 1 to 3 carbon atoms or alkenyl group having 2 or 3 carbon atoms and p equals 0 to 5 and s equals 0 or 1.

Compounds of the present invention which are asymmetrical around the linking group (i.e., wherein y and z are different in number) can be prepared by a two-step process, wherein the first step involves coupling a compound of the formula:

$$B-(NHCO)_x-\underset{R_2}{Het}-(NHCO-\underset{R_3}{Het})_y-NH_2$$

wherein B, x and z are as defined above, with a dicarboxylic acid of the formula:

$$X-R_1-X$$

wherein $R_1$ and X are as defined above (this coupling is generally with the use of equimolar amounts of the reactants). This is followed by coupling of a compound of the formula:

$$B-(NHCO)_x-\underset{R_5}{Het}-(NHCO-\underset{R_4}{Het})_z-NH_2$$

wherein B, x and z are as defined above, with the provisions that z is different than y.

According to preferred embodiments of the invention, the following reaction schemes demonstrate preferred chemical pathways to the compounds of this invention having the various desired end groups:

A - Preparation of Amidinium End Group

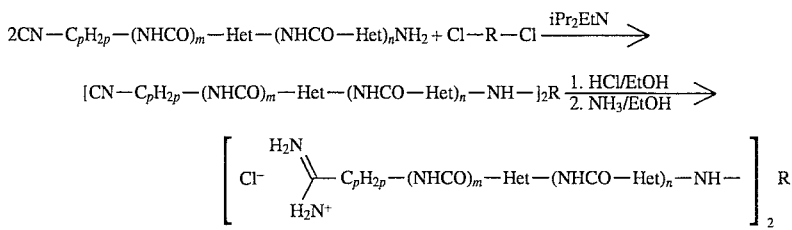

B - Preparation of Guanidinium End Groups

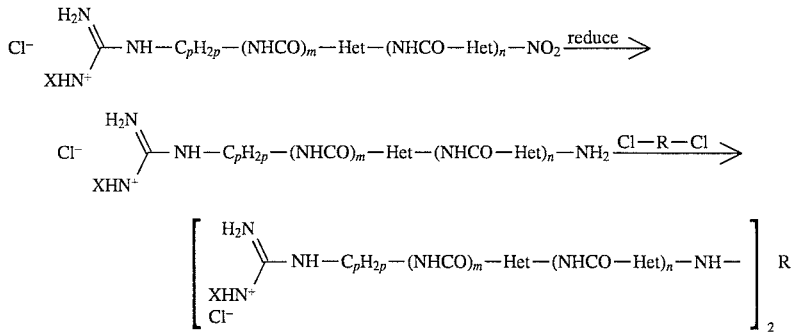

C - Preparation of Ammonium Salt in End Group

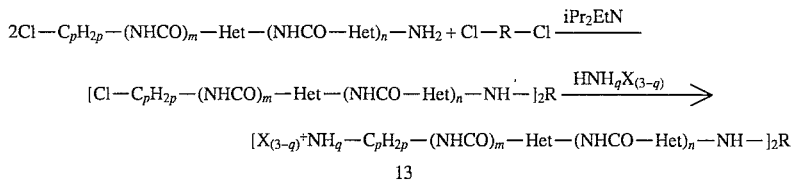

D - Preparation of Sulfonium Salts

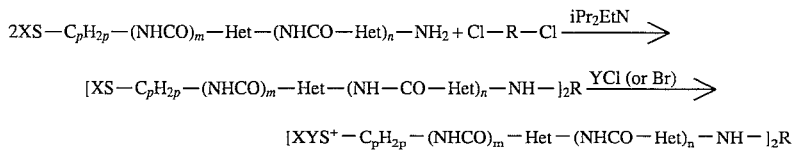

Reference may be made to J. W. Lown and K. Krowicki, *J. Org. Chem.* 1985, 50 3774 regarding the synthesis of related types of pyrrole moieties such as the synthesis of distamycin. The general synthesis of the compounds according to this invention are based on the total synthesis of distamycin. Dipyrrole or tripyrrole peptides bearing an amino group and a side-chain containing a group (B) which is the nitrile, ammonium or sulfide as represented by the following formula:

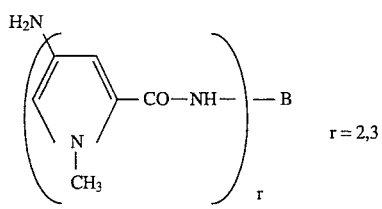

are allowed to react at a temperature of −35° to +10° C., preferably about −20° C., with a dicarboxylic acid dichloride in the presence of a base or with a diimidazolide of a dicarboxylic acid to give a bis-amide of the dicarboxylic acid. The resulting compound in the case of nitrile is allowed to react at a temperature of 0° to +35° C., preferable +15° to +25° C., more preferably about +20° C., with ethanol in the presence of hydrochloric acid and then at a temperature of 0° to +35° C., preferably +15° to +25° C., more preferably about +20° C., with ammonia (Pinner reaction) to generate an amidinium moiety in the final product, as exemplified by the above reaction scheme A. As with reaction scheme D, the sulfide is methylated at a temperature of 0° to +35° C., preferable +15° to +25° C., more preferably about +20° C., to produce the corresponding sulfonium salt.

The compounds of formula I, are useful as antiretroviral agents, especially against the Human Immunodeficiency Virus (HIV). Human patients suffering from diseases caused by, for example, HIV, can be treated by administering to the patient a pharmaceutically effective amount of one or more of the present compounds optionally, but preferably in the presence of a pharmaceutically acceptable carrier or diluent. There may be also included pharmaceutically compatible binding agents and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, rectally or topically, in a liquid or solid form. For injection purposes, the medium used may be a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethylsulfoxide, complex forming agents (for example, ethylenediamine tetracetic acid), high molecular weight polymers (for example, liquid polyethylene oxide) for viscosity regulation or polyethylene derivatives of sorbitan anhydrides. Solid carrier materials include, for example, starch, lactose, mannitol, methylcellulose, talc, highly dispersed silicic acid, high molecular weight fatty acids (such as stearic acid), gelatin, agar, calcium phosphate, magnesium sterate, animal and vegetable fats or solid high molecular weight polymers (such as polyethylene glycol). Compositions suitable for oral administration can, if desired, contain flavoring and/or sweetening agents.

A preferred mode of administration of the compounds of this invention is oral. Accordingly, the compounds may be formulated into capsule form or tablet form.

The active materials according to the present invention can be employed in dosages and amounts which are conventional in the art. Thus, the materials can be used at a dosage range in humans of from about 1 to 200 mg/kg total body weight/day. A more preferred range lies between 1–30 mg/kg total body weight/day. The dosages may be administered at once, or may be divided into a number of smaller doses to be administered at varying intervals of time.

The in vitro anti-HIV screening test results, performed at the United States National Cancer Institute, have shown that 23 of the present compounds are active. Of the fifteen, ten are considered "active", and thirteen are determined "moderately active". Certain of the compounds screened for anti-AIDS activity at the NCI were determined to be "inactive". These compounds were ones wherein the $R_1$ is —CO—$(CH_2)_6$—CO— or —CO—$(CH_2)_8$—CO—, A is amidine, x is 1, Hew is methylpyrrole, and y and z are 1, as well as compounds 9, 11, 15, 16, 18 and 37.

The therapeutic index of a compound is determined by dividing the inhibitory or lethal concentration for 50% of the population ($IC_{50}$) by the effective concentration for 50% of the population ($EC_{50}$). The therapeutic indexes for the particularly active compounds of the present invention range from 1.46 to 161.

As used in this invention, antiretroviral activity refers to the ability of a compound to inhibit the growth of a retrovirus. The retrovirus of primary importance with respect to the present invention is HIV. However, the present compounds may also exhibit antiretroviral activity towards other retroviruses as would be apparent by the suspected mechanism of action and other viruses which replicate or exhibit reverse transcription.

The compounds of the present invention should also be therapeutically effective in the treatment of hepatitis B viral infection in mammals, especially humans. Similar to retroviruses (including HIV-1), the hepatitis B virus replicates by reverse transcription. In addition, hepatitis B virus putative viral polymerase share amino acid homology with reverse transcriptase of retroviruses and a comparison of the thirteen (13) hepadnavirus isolates determined that other conserved areas showing homology to corresponding regions of Type c retro virus. Miller et al., Proc. Natl. Acad. Sci. USA, Vol 83:2531–2535 (1986).

Since it is theorized that the activity of the compounds of the present invention may be due to the compounds binding with nucleic acid sequence(s) associated with the cellular action of retroviruses to inactivate such nucleic acids which code for the retroviral activity, the compounds are likely to inhibit binding with nucleic acid sequence(s) of the hepatitus B virus associated with the cellular action of reverse transcription to inactivate such nucleic acids which code for the retroviral-like activity. Therapeutically effective anti-hepatitus B dosages would be the same as anti-HIV-1 dosage levels as well as would the routes of administration.

The ability of a compound to inhibit HIV may be measured by various experimental techniques. One such technique, currently employed by the United States National Cancer Institute to screen potential anti-HIV compounds, involves the inhibition of the killing of HIV-infected $T_4$ lymphocytes. Compounds of the present invention have been tested for anti-HIV-1 activity in the NCI protocol; however, one skilled in the art would appreciate that the compounds should exhibit activity against HIV-2 as well.

Preferred embodiments of the invention are exemplified in the following Examples which are in no way to be construed as limiting the scope of the appended claims.

EXAMPLE 1

Compound of the formula I, where x=1, y and z each are 1;

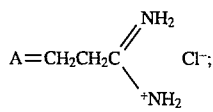

$R_1$ equals —COCH$_2$CH$_2$CO—, was prepared. 1-Methyl-4-(1-methyl-4-aminopyrrole-2-carboxamido)-pyrrole-2-carboxamidopropionitrile (105 mg, 0.33 mmole) and 1-Pr$_2$EtN (diisopropylethylamine) (65µl, 0.16 mmole) in anhydrous THF (1 ml) was added and the mixture was allowed to reach room temperature. The solvents were evaporated to dryness and water was added. The resulting solid was collected and washed with hot MeOH to give 90 mg (77% yield) of the product m.p. 297° C. The latter was suspended in anhydrous EtOH and saturated with HCl while cooling. After 1.5 hours at room temperature, the solvent was removed in vacuo and the residue was washed with dry ether then ethanol was added followed by some ammonia condensed into the solution. After 1 hour at room temperature, the solvent was removed and the residue was washed with MeOH, EtOH and hexane to afford 80 mg of a solid. Recrystallization from a small volume of water gave a jelly-like precipitate which was washed with EtOH, hexane and dried to give 35 mg (35% yield) of pure product m.p. 283°–285° C. dec. $^1$H-NMR (DSMO-d$_6$): δ2.60 (m, 4H), 3.60 (m, 2H), 3.83 (s, 6H), 6.92 (d, 2H), 7.18 (d, 2H), 8.25 (t, 1H), 8.70 (bs, 2H), 9.02 (bs, 2H), 9.93 and 9.97 (2s, 2H), MS-FAB (m/z):745 (M-Cl-HCl)$^+$: Anal. Calcd. for C$_{34}$H$_{46}$Cl$_2$N$_{14}$O$_6$: C, 49.9, H. 5.7, N, 24.0, Cl, 8.7, Found: C, 50.3, H, 6.05, N, 22.9, Cl, 8.7.

EXAMPLE 2

Compound of the formula I, where x equals 1; y and z are each equal to 1;

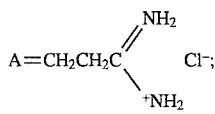

$R_1$ equals —CO— was prepared. 1-Methyl-4-(1-methyl-4-aminopyrrole-2-carboxamido)-pyrrole-2-carboxamidopropionitrile (315 mg, 1 mmole) and 81 mg of 1,1'-carbonyldiimidazole were dissolved in 10 ml of anhydrous $CH_3CN$ and refluxed under argon for 5 minutes. A solid forms which was collected to give 302 mg (88.6% yield) of the pure product was treated with HCl in EtOH and then $NH_3$ (as in Example 1). After the reaction was completed, the mixture was decanted from an insoluble residue. The solvent was removed in vacuo and the residue was dissolved in 4 ml of MeOH and an excess of $CH_3CN$ was added to precipitate the product which was collected and washed with 1 ml of cold water whereupon it became jelly-like. The product was redissolved in MeOH and reprecipitated with $CH_3CN$ to give 216 mg (57% overall yield) of the pure compound m.p. 211°–215° C.; $^1$H-NMR (DMS)-$d_6$): δ2.64 (t, 2H), 3.52 (q, 2H), 3.84 (s, 6H), 6.82, 6.94, 7.03, 7.20 (4d, 4H), 8.25 (t, 1H), 8.73 (2s, 3H), 9.05 (s, 2H), 9.88 (s, 1H), MS-FAB: 690 (M-Cl-HCl)$^+$. Anal. Calcd. for $C_{31}H_{42}Cl_2N_{14}O_5$: C, 48.9, H, 5.6, Cl, 9.3, N, 25.7; Found C, 48.5, H, 5.7, Cl, 9.7, N, 25.3.

EXAMPLES 3(A) AND (B)

The following Examples illustrate the effect of altering the steric size of the terminal group (in these cases trialkylammonium) on the basic Hew block of the general formula on the nucleic acid binding and antiviral efficacy. The effects were demonstrated on deoxyribonucleic acid to show that steric hindrance in the terminal group in DNA binding generally reduces antiviral activity of the compounds.

(A) 1-Methyl-4-(1-methyl-4-trimethylammoniumacetamidopyrrole-2-carboxamido)pyrrole-2-carboxyamidopriopionamidine chloride hydrochloride A solution of the precursor 1-methyl-4-(1-methyl-4-trimethylammonium-acetamido-pyrrole-2-carboxamido)pyrrole-2-carboxyamidopriopionitrile chloride (347 mg, 0.07 mmoles) in 5 ml of absolute ethanol was treated with dry hydrogen chloride with cooling. After 2 hours, the solvent was removed in vacuo, 5 ml of absolute ethanol was added and dry $NH_3$ gas passed into the solution. The solid dissolved during 2 hours at room temperature, then the solution was evaporated to dryness and extracted with hot isopropyl alcohol (100 ml). The extract was concentrated to ca. 10 ml, acetone added and the resulting precipitate collected, washed with acetone, and dried to vacuo to give the product, 300 mg (85% yield) as an amorphous hygroscopic solid, no definite m.p.; $^1$H-NMR (DMSO-$d_6$): δ2.67 (t, 2H), 3.31 (s, 9H), 3.52 (q, 2H), 3.82 and 3.87 (2s, 6H), 4.44 (s, 2H), 6.97 (d, 1H), 7.02 (d, 1H), 7.24 (d, 1H), 7.29 (d, 1H), 8.31 (t, 1H), 8.82 (bs, 2H), 9.72 (bs, 2H), 10.06 (s, 1H), 11.23 (s, 1H), IR (Nujol) $v_{max}$: 1260, 1377, 1405, 1453, 1531, 1582, 1643, 1685, 3247 cm$^{-1}$; MS-FAB (m/z) 430 (M-HCl-Cl)$^+$.

Sulfate. The sulfate corresponding to the product was prepared in order to obtain an analytically pure sample by precipitation from a methanolic solution of the above compound by means of a large excess of tetraethylammonium sulfate, m.p. 295° C.: IR (Nujol) $v_{max}$: 1255, 1377, 1405, 1462, 1525, 1560, 1580, 1640, 1670, 3280 cm$^{-1}$; MS-FAB (m/z) 431 (M-HSO$_4$)$^+$, 529 MH$^+$; Anal. Calcd. for $C_{20}H_{32}N_8O_7S$ (528.59), C, 45.4, H, H, 6.1, N, 21.1, S, 6.1. Found: C, 45.0, H, 6.0, N, 20.7, S, 5.8.

(B) 1-Methyl-4-(1-methyl-4-trimethylammoniumacetamidopyrrole-2-carboxamido)pyrrole-2-carboxyamidopriopionamidine chloride hydrochloride A solution of the precursor analogous to that of Example 3(A) (173 mg, 035 mmoles) in 10 ml of absolute ethanol was treated with dry hydrogen chloride with cooling. After 2 hours, the solvent was removed in vacuo and the residue dissolved in 10 ml of absolute ethanol and treated with an excess of dry ammonia. After 2 hours at room temperature, the solvent was removed in vacuo and the residue dissolved in 5 ml of isopropyl alcohol; then the product was precipitated with ether. The solid was collected, washed with ether and dried at 100° in vacuo to afford the product 103 mg (59% yield) m.p. 180° (dec); $^1$H-NMR (DMSO-$d_6$): δ1.32 (t, 9H), 2.67 (t, 2H), 3.54 (m, 8H), 3.83 and 3.88 (2s, 6H), 4.32 (s, 2H), 6.96 (d, 1H), 7.01 (d, 1H), 7.21 (d, 1H), 7.30 (d, 1H), 8.28 (t, 1H) 8.80 and 9.10 (bs, 4H), 10.03 (s, 1H), 11.47 (s, 1H), IR (Nujol): 1376, 1404, 1462, 1531, 1581, 1646, 1684, 3250 cm$^{-1}$; MS-FAB (m/z): 981 (2M-HCl-Cl)$^+$, 473 (M-HCl-Cl)$^+$.

The activities of Examples 3(A) and 3(B) expressed as minimum inhibitory concentration (μg/ml) against vaccinia virus were 20 and 300 respectively illustrating the effects of steric hindrance in DNA binding on reducing agent activity. The larger the terminal group, as demonstrated by compound 3(B), the lesser the activity: hence the terminal group is of a selected size which will maintain nucleic acid sequence bonding desired antiretroviral activity.

The compound numbers referred to in the following examples correspond to the numbered structures in the "Detailed Description of the Invention" section.

EXAMPLE 4

(A) 1-Methyl-4-[1-methyl-4-(1-methyl-4-aminopyrrole-2-carboxamido)pyrrole-2-carboxamido]pyrrole-2-carboxamidopriopionitrile (Intermediate Compound)

1-Methyl-4-[1-methyl-4-(1-methyl-4-aminopyrrole-2-carboxamido)pyrrole-2-carboxamido]pyrrole-2-carboxamidopriopionitrile (Lown, W. J. and Krowicki, K., J. Org. Chem. Vol. 50, p. 3774 (1985) and Krowicki, K. and Lown, W. J., J. Org. Chem., Vol. 52, p. 3493 (1987) (420 mg, 0.9 mmol) was reduced over 5% palladium on charcoal (260 mg) in a mixture of DMF (15 ml) and methanol (5 ml) at 45°. After the reduction the solvents were evaporated under reduced pressure. The residue was dissolved in a small amount of acetonitrile (2 ml) and an excess of ethyl acetate (20–30 ml) as added to precipitate some impurities. The filtrate was treated with an excess of hexane to precipitate a white pure product 9 (250 mg, 63.5% yield), m.p. 155°–160°. $^1$H-NMR (DMSO-$d_6$): δ2.74 (t, 2H), 3.42 (Q, 2H), 3.76 (s, 3H), 3.85 and 3.87 overlapped with a bs (3s, 8H), 6.27 (d, 1H), 6.40 (d, 1H), 6.95 (d, 1H), 7.04 (d, 1H), 7.24 (2d, 2H), 8.37 (t, 1H) 9.66 (s, 1H), 9.96 (s, 1H); IR (nujol): 1260, 1377, 1403, 1464, 1529, 1582, 1646, 2245, 3120, 3310 $cm^{-1}$; MS m/z 436.1981 (calcd. 436.1983). Analysis Calcd. for $C_{19}H_{26}ClN_6O_3$: C 52.3, H 6.0, Cl 8.1, N 22.5. Found: C 52.3, H 6.0, Cl 7.9, N 22.0.

EXAMPLE 5

(A) N,N'-Di(1-methyl-2-[1-methyl-2-carboxamido (3-proprionitrile)-4-pyrrole]-4-pyrrolyl)succinamide The intermediate compound (105 mg, 0.33 mmol) and i-$Pr_2$EtN (65 μL, 0.37 mmol) were dissolved in anhydrous acetonitrile (5 ml) and cooled to −20° C. Succinyl chloride (18 μL, 0.16 mmol) in anhydrous THF (1 ml) was added. The mixture was allowed to reach ambient temperature. The solvents were evaporated to dryness, water was added, and the resulting solid was collected and washed with hot MeOH. The product was dissolved in DMF and when placed on a TLC plate (SiO$_2$) with CHCl$_3$+15% MeOH system it gave one spot. For analytical purposes, the product was purified by dissolution in a small amount of DMF and precipitation with a large amount of EtOH to give 90 mg (77%) of 15 m.p. 292°. $^1$H-NMR (DMSO-d$_6$): δ2.58 (s, 4H) 2.74 (t, 4H), 3.42 (q, 4H), 3.83 (2s, 12H), 6.86, 6.93, 7.17 and 7.22 (4d, 2H each), 8.35 (t, 2H), 9.89 (s, 4H); IR (nujol): 1376, 1401, 1447, 1465, 1511, 1535, 1585, 1645, 2245, 3120, 3304 cm$^{-1}$; MS (m.z. rel. int.): 396.1543 (9.98) for C$_{19}$H$_{20}$N$_6$O$_4$ which is (O=C=CH—M$_{1/2}$)$^+$. Analysis Calcd. for C$_{34}$H$_{38}$N$_{12}$O$_6$: C 57.5, H 5.4, N 23.6. Found: C 57.8, N 5.4, N 23.3.

(B) N,N'-Di(1-methyl-2-[1-methyl-2-carboxamido(3-proprionamidine)-4-pyrrole[-4-pyrrolyl)succinamide dihydrochloride (Compound 5)

A suspension of the previous product (130 mg, 0.18 mmol) in 15 ml anhydrous EtOH was saturated with HCl with cooling. After 1.5 hr. at r.t., the solvent was evaporated under reduced pressure. The residue was washed with dry ether, then ethanol was added followed by some NH$_3$ condensed into the vessel. After 1 hr at r.t. the solvents were removed and the residue was washed with MeOH, EtOH and hexane to give 116 mg of a solid. The latter was examined by TLC (SiO$_2$) with MeOH and a drop of formic acid and indicated formation of the product (Rf=0.3) containing some more polar impurity. Recrystallization from a small amount of water gave a gel-like precipitate which was washed with EtOH and hexane and dried give to 50 mg (34% of pure 5a, m.p. 283°–5° dec. $^1$H-NMR (DMSO-d$_6$): δ2.60 (m, 8H) 3.50 (m, 4H), 3.83 (s, 12H), 6.92 (d, 4H), 7.18 (d, 4H), 8.25 (t, 2H), 8.70 (bs, 4H), 9.02 (bs, 4H) 9.93 and 9.97 (2s, 4H); IR (nujol): 1352, 1377, 1464, 1521, 1576, 1638, 1700, 3260 cm$^{-1}$; MS-FAB (m/z): 745 (M-Cl-HCl)$^+$. Analysis Calcd. for C$_{34}$H$_{46}$Cl$_2$N$_{14}$O$_6$: C 49.94, H 5.67, N 23.98, Cl 8.67. Found: C 50.3, H 6.05, N 22.90, Cl 8.75.

EXAMPLE 6

(A) N,N'-Di(1-methyl-2-[1-methyl-2-carboxamido(3-proprionitrile)-4-pyrrole]-4-pyrrolyl)malonamide The intermediate compound (315 mg, 1 mmol), malonic acid (52 mg, 0.5 mmol) and DCC 206 mg, 1 mmol) were stirred in acetonitrile (6 ml) for 2 hr at room temperature and finally the mixture was heated briefly to boiling to complete the reaction. A solid which contained dicyclohexylurea was collected and the filtrate was extracted with DMF. The DMF solution was treated with water and the solid formed was recrystallized from a mixture of acetonitrile (2 ml) and methanol (2 ml) to give pure compound (140 mg, 40% yield), m.p. 225°–30°. $^1$H-NMR (DMSO-d$_6$): δ2.73 (t, 2×2H), ¯2.40 (q+s overlapped, 2×2H+2H), 3.83 and 3.86 (2s, 2×6H), 6.91 (2d, 2×2H), 7.18 and 7.22 (2d, 2×2H), 8.35 (t, 2×1H), 9.91 (s, 2×1H), 10.09 (s, 2×1H); IR (nujol): 1200, 1264, 1290, 1376, 1401, 1464, 1511, 1532, 1585, 1638, 1662, 2250, 3120, 3305 cm$^{-1}$; MS-FAB (m/z): 697 (MH$^+$). Analysis Calcd. for c$_{33}$H$_{36}$N$_{12}$O$_6$: C 56.9, H 5.2, N 24.1. Found: C 56.6, H 5.4, N 23.9.

(B) N,N'-Di(1-methyl-2-[1-methyl-2-carboxamido(3-proprionamide)-4-pyrrole]-4-pyrrolyl)malonamide dihydrochloride (Compound 4)

The compound of the previous synthesis (160 mg, 0.23 mmol) was suspended in dry ethanol and the mixture was saturated with dry halogen chloride. After 1.5 hr at room temperature, the solvent was removed under reduced pressure. The residue was treated with dry ethanol and dry ammonia. After 1 hr the solution was decanted from undissolved material and evaporated to dryness. The residue was dissolved in 2 ml of boiling water and an excess of acetonitrile was added to the hot solution. The precipitate was collected and washed with a small amount of water. The operation was repeated and pure compound 4 was collected, 100 mg (59% yield), m.p. 218°–224°. The compound, if crystallized from water, precipitates in the form of a jelly. $^1$H-NMR (DMSO-d$_6$): δ2.63 (t, 2>2H), ¯3.35 (s overlapped with the peak of water), 3.50 (q, 2×2H), 3.80 and 3.83 (2s, 2×6H), 6.93 (s, 2×2H), 7.20 (s, 2×2H), 8.26 (t, 2×1H), 8.90 (bs, 2×4H), 9.96 (s, 2×1H), 10.28 (s, 2×1H). D$_2$O exchange experiment showed the presence of malonyl protons at δ3.30. IR (nujol): 1260, 1377, 1405, 1463, 1535, 1580, 1645, 3100, 3270 cm$^{-1}$; MS-FAB (m/z) 731 (M-Cl-HCl)$^+$. Analysis Calcd. for C$_{33}$H$_{44}$N$_{14}$O$_6$Cl$_2$: C 49.3, H 5.5, N 24.4, Cl 8.8. Found: C 49.0, H 5.7, N 27.0, Cl 9.0.

EXAMPLE 7

(A) N,N'-Di(1-methyl-2-[1-methyl-2-carboxamido(3-proprionitrile)-4-pyrrole]-4-pyrrolyl)urea The intermediate compound (365 mg, 1.16 mmol) and 1,1'carbonyldiimidazole (94 mg, 0.58 mmol) were allowed to react in boiling acetonitrile (3 ml). A solid which formed was collected, washed with acetonitrile to give 350 mg (88.6% yield) of pure product, m.p. 296°–7°. $^1$H-NMR 3.88 (s, 6H), 6.80 (d, 2H), 6.92 (d, 2H), 7.02 (d, 2H), 7.21 (d, 2H), 8.12 (s, 2H), 8.25 (t, 2H), 9.81 (s, 2H); IR (nujol): 1199, 1217, 1252, 1378, 1409, 1436, 1465, 1504, 1544, 1589, 1621, 1653, 1672, 2240, 3270, 3424 cm$^{-1}$; MS-FAB (m/z): 655 (MH$^+$). Analysis Calcd.: C 56.9, H 5.2, N 25.7. Found: C 56.6, H 5.4, N 25.5.

(B) N,N'-Di(1-methyl-2-[1-methyl-2-carboxamido(3-propionamidine)-4-pyrrole]-4-pyrrolyl)urea dihydrochloride (Compound 3)

The compound synthesized in the previous step (116 mg, 0.25 mmol) was suspended in dry ethanol and the solution saturated with HCl. After 2 hr the solvent was evaporated in vacuo and the residue treated with dry ammonia in ethanol for 1 hour. The mixture was decanted from an insoluble residue and the solution evaporated to dryness. The residue was dissolved in 2 ml of methanol and an excess of acetonitrile was added to precipitate the product. The latter was collected and washed with 1 ml of water when it became jelly-like. It was redissolved in methanol and precipitated with acetonitrile to give the compound (3) (117 mg, 61.6% yield), m.p. 211°–215°. $^1$H-NMR (DMSO-d$_6$): δ2.64 (t, 4H), 3.52 (q, 4H), 3.84 (2s, 12H), 6.82 (d, 2H), 6.94 (d, 2H), 7.03 (d, 2H), 7.20 (d, 2H), 8.73 (2s overlapped, 6H), 9.05 (s, 4H), 9.88 (s, 2H); IR (Nujol): 1264, 1377, 1402, 1439, 1489, 1531, 1583, 1640, 1689, 3088, 3279 cm$^{-1}$; MS-FAB (m/z): 690 (M-Cl-HCl)$^+$. Analysis Calcd. for C$_{31}$H$_{42}$Cl$_2$N$_{14}$O$_5$: C 48.9. H 5.6, Cl 9.3, N25.7. Found: C 48.5, H 5.7, Cl 9.7, N 25.3.

EXAMPLE 8

(A) N,N'-Di(1-methyl-2-carboxamido(3-proprionitrile)-4-pyrrole]-4-pyrrolyl)apidamide Adipic acid (29.2 mg, 0.2 mmol) in acetonitrile (0.5 ml) was treated with pivaloyl chloride (50 μL, 0.4 mmol) and Hunig's base (160 μL, 0.9 mmol) and then compound 7 (126 mg, 0.42 mmol) in DMF (0.5 ml) was added. After a half hour at room temperature the mixture was evaporated to dryness under reduced pressure. The residue was washed with water and hot acetonitrile. The solid was dissolved in hot DMF and precipitated with an excess of acetonitrile to give the compound (95 mg, 61% yield), m.p. 244°–46° dec. $^1$H-NMR (DMSO-d$_6$): δ1.60 (s, 4H), 2.27 (s, 4H), 2.74 (t, 4H), 3.40 (q, 4H), 3.83 (2s, 12H), 6.93 (s, 2H), 7.17 (s, 2H), 7.22 (s, 2H), 8.38 (t, 2H), 9.82 (s, 2H), 9.91 (s, 2H: IR (Nugol): 1376, 1400, 1464, 1513, 1533, 1585, 1641, 2258, 3294 cm$^{-1}$; MS-FAB (m/z): 738 (M$^+$), 739 (MH$^+$); Analysis Calcd. C 58.5, H 5.7, N 22.7. Found: C 58.9, H 5.9, N 22.5.
(B) N,N'-Di(1-methyl-2-[1-methyl-2-carboxamido(3-proprionamidine)-4-pyrrole]-4-pyrrolyl) adipamide dihydrochloride (Compound 7)

The compound synthesized in the previous step (320 mg, 0.43 mmol) was treated under Pinner reaction conditions as in Example 3 above. After evaporation of solvents, water (3.5 ml) was added and a crystalline substance was collected to give (7) (215 mg, 58.7% yield), m.p. 195°–6°. $^1$H-NMR (DMSO-d$_6$): δ1.60 (s, 4H), 2,27 (s, 4H), 2.62 (t, 4H), 3.52 (q, 4H), 3.80 (2s, 12H), 6.88 (d, 2H), 6.95 (d, 2H), 7.18 and 7.20 (2d, 4H), 8.25 (t, 2H) 8.70 (s, 4H), 9.00 (s, 4H), 9.00 (s, 4H), 9.92 (s, 2H): IR (Nujol): 1208, 1261, 1377, 1404, 1463, 1531, 1579, 1641, 1691, 3256 cm$^{-1}$; MS-FAB m/z 773 (M-HCl-Cl)$^+$; Analysis Calcd.: C 51.1, H 6.0, N 23.2, Cl 8.4. Found: C 50.9, H 6.2, N 23.6, Cl 8.8.

EXAMPLE 9

(A) N,N'-Di(1-methyl-2-[1-methyl-2-carboxamido(3-propionitrile)-4-pyrrole]-4-pyrrolyl)malemide The intermediate compound (158 mg, 0.5 mmol) and maleic anhydride (49 mg, 0.5 mmol) were heated in acetonitrile (5 ml) at 50° for 3 minutes. Another portion of the intermediate compound (158 mg) was added and the solution was evaporated to dryness. The residual solid was dissolved in DMF (2 ml) and DCC (103 mg, 0.5 mmol) was added, and the mixture was set aside overnight at room temperature. Two drops of water were added and the solution was filtered. Then an excess of water precipitated the crude product. The product was collected and chromatographed on silica gel with chloroform and 15% of methanol providing yellow fractions. These were combined and evaporated, and the residue recrystallized from acetone to give the product (100 mg, 56.5% yield), m.p. 250°–2°. Analytical data for this and related compounds is given in Table I.
(B) N,N'-Di(1-methyl-2-carboxamido(3-(proprionamidine-4-pyrrole]-4-pyrrolyl)maleamide dihydrochloride (Compound 14)

The product obtained in the previous step (170 mg, 0.24 mm) was treated under Pinner reaction conditions as in Example 3. The completed reaction mixture was evaporated to dryness and the residue dissolved in ethanol. Controlled addition of isopropanol provided selective precipitation of impurities. The mother liquor was evaporated and the residue was dissolved in methanol and precipitation with acetonitrile gave pure compound (14) (166 mg, 85% yield), m.p. 217°.

EXAMPLE 10

(A) N,N'-Di(1-methyl-2-[1-methyl-2-carboxamido(3-proprionitrile)-4-pyrrole]-4-pyrrolyl)transcyclopropyldicarboxamide (Compound 8a)

The synthesis and characterization of compounds 3, 4 and 5 have been reported (Krowicki, K. et al, J. Med. Chem., Vol. 31, p. 341 (1988)). Transcyclopropyldicarboxylic acid (59 mg, 0.45 mmole) and 1,1'-carbonyldiimidazole (146 mg, 0.7 mmole) in acetonitrile (2.5 ml) were heated under reflux until the evolution of carbon dioxide ceased. To the cooled solution the appropriate amine (284 mg, 0.9 mmole) and 0.8 ml of DMF were added and the mixture was stirred for 2 hr at room temperature (the product partially precipitated) and was evaporated to dryness under reduced pressure. The residue was washed with acetonitrile, aqueous K$_2$CO$_3$ then water to give 8a, 289 mg (88.6% yield) m.p. 312° dec.
(B) N,N'-Di(1-methyl-2-[1-methyl-2-carboxamide-(3-proprionamidine)-4-pyrrole]-4-pyrrolyl)transcylcopropyldicarboxamide dihydrochloride (Compound 8b)

Compound 8a (216 mg, 0.3 mmole) was treated under Pinner reaction conditions as described previously. The final reaction mixture was evaporated to dryness and the residue was extracted with hot propanol (150 ml). The extract was evaporated to dryness and the residue dissolved in methanol 1 ml, and an excess of acetonitrile was added to precipitate the product 8b, 170 mg (68.5% yield) m.p. 210° (softens).

EXAMPLE 11

Commercially available acid chlorides for the linker groups were used directly without further purification. Otherwise, the appropriate acid chlorides were prepared from the acids according to the following procedure: An acid and a drop of dimethylformamide was heated in thionyl chloride (5 to 10 mole in excess) to 55°–65° C. for 30 to 45 min until a homogeneous liquid was obtained. The excess of the chlorinating agent was removed by evaporation. A small amount of methylene chloride was added to the crude acid chloride then evaporated. The diacid dichloride was then dissolved in methylene chloride or THF and aliquots were taken and used for coupling reactions.

EXAMPLE 12

Distamycin A (50 mg, 0.09 mmol) was dissolved in 4 mL of methanol. To this yellow solution was added 100 μL of concentrated hydrochloric acid. The solution was stirred for 6–8 h and the reaction progress was followed by TLC (methanol:acetic acid, 100:5). The solvent was evaporated and the crude product was redissolved in methanol and precipitated with ether. The product was recrystallized in this way twice more. The supernatant was decanted and the residual solid was dried in vacuo. The final product was obtained as an off-white solid 50 mg (89% yield).

EXAMPLE 13

Bis-distamycin (Compound 15)

A solution of succinyl dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 μL, 0.09 mmol) in 3 mL of dimethylformamide cooled to 0° C. After 10 min, a solution of Hunig's base (16 μL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 68% yield. m.p. 210° C.; $^1$H-NMR, 2.48 (COCH$_2$CH$_2$CO, 4H, s), 2.56 [2×CH$_2$C(NH$_2$)$_2$Cl, 4H, tr, J=6 Hz], 3.50 (2×CONHCH$_2$, 4H, q, J=6 Hz), 3.80 (2×NCH$_3$, 6H, S), 3.82 (2×NCH$_3$, 6H, s), 3.83 (2×NCH$_3$, 6H, s), 6.90 (2×py-CH, 2H, d, J=2 Hz), 6.94 (2×py-CH, 2H, d, J=2 Hz), 7.04 (2×py-CH, 2H, d, J=2 Hz), 7.14 (2×py-CH, 2H, D, J=2 Hz), 7.18 (2×py-CH, 2H, d, J=2 Hz), 7.22 (2×py-CH, 2H, d, J=2 Hz), 8.24 (2×CONHCH$_2$, 2H, tr, J=6 Hz), 8.74

[2×C(NH$_2$)$_2$Cl, 4H, s], 9.04 [2×C(NH$_2$)$_2$Cl, 4H, S], 9.93 (5×py-NHCO, 5H, s), 9.96 (py-NHCO, 1H, s); MS (FAB), 989 (M-2×Cl-H, 0.34).

EXAMPLE 14

Bis-distamycin (Compound 16)

A solution of hexan-1,6-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 78% yield. m.p., 210° C.; $^1$H-NMR, 1.28 (4,5-suber-CH$_2$, 4H, m), 1.57 (3,6-suber-CH$_2$, 4H, m), 2.23 (2m7-suber-CH$_2$, 4H, tr, J=7 Hz), 2.63 (2×C$\underline{H}_2$C(NH$_2$)$_2$Cl, 4H, tr, J=6 Hz], 3.49 (2×CONHC$\underline{H}_2$, 4H, m), 3.80 (2×NCH$_3$, 6H, s), 3.81 (2×NCH$_3$, 6H, s), 3.83 (2×NCH$_3$, 6H, s), 6.88 (2×py-CH, 2H, d, J=2Hz), 6.94 (2×py-CH, 2H, d, J=2Hz), 7.05 (2×py-cH, 2H, d, J=2 Hz), 7.15 (2×py-CH, 2H, d, J=2 Hz), 7.18 (2×py-CH, 2H, d, J=2 Hz), 7.23 (2×py-CH, 2H, d, J=2 Hz), 8.25 (2×CONHCH$_2$, 2H, m), 8.72 [2×C(NH$_2$)$_2$Cl, 4H, s], 9.03 [2×C(NH$_2$)$_2$Cl, 4H, s], 9.86 (2×py-NHCO, 2H, s), 9.92 (4×py-NHCO, 4H, s); MS (FAB), 1045 (M-2×Cl-H, 0.38).

EXAMPLE 15

Bis-distamycin (Compound 17)

A solution of octan-1,8-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min. a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 65% yield. m.p., 198°–202° C.; $^1$H-NMR, 1.26 [(4,5,6, 7-seba-CH$_2$, 8H, m), 4H, tr, J=6 Hz], 1.55 [(3,8-seba-CH$_2$), 4H, m], 2.22 (2,9-seba-CH$_2$), 4H, tr, J=8 Hz], 2.61 [2×C $\underline{H}_2$C(NH$_2$)$_2$Cl, tr, J=6 ], 3.48 (2×CONHC$\underline{H}_2$, 4H, m), 3.80 (2×NCH$_3$, 6H, s), 3.81 (2×NCH$_3$, 6H, s), 3.83 (2×NCH$_3$, 6H, s), 6.89 (2×py-CH, 2H, d, J=2Hz) 6.95 (2×ph-CH, 2H, d, J=2 Hz), 7.05 (2×py-CH, 2H, d, J=2 Hz), 7.15 (2×py-CH, 2H, d, J=2 Hz), 7.18 (2×py-CH, 2H, d, J=2 Hz), 7.22 (2×py-CH, 2H, d. J=2 Hz), 8.23 (2×CONHpy-2H, m), 8.65 [2×C(NH$_2$)$_2$Cl, 4K, s], 8.99 [2×C(NH$_2$)$_2$Cl, 4H, s], 9.82 (2×py-NHCO, 2H, s), 9.91 (4×py-NHCO, 4H, s); MS (FAB), 1074 (m-2×Cl-H, 0.08).

EXAMPLE 16

Bis-distamycin (Compound 18)

A solution of docosane-1,22-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 73% yield. m.p., 215° C.; $^1$H-NMR, 1.23 (4,5, . . . 20,21-tetraco-CH$_2$, 36H, s), 1.55 (3,22-tetraco-CH$_2$, 4H, m), 2.21 (2,23-tetraco-CH$_2$, 4H, tr, J=7 Hz), 2.62 [2×C $\underline{H}_2$C(NH$_2$)$_2$Cl, 4H, tr, J=6 Hz], 3.50 (2×CONHC$\underline{H}_2$, 4H, tr, J=6 Hz), 3.80 (2×NCH$_3$, 6H, s), 3.82 (2×NCH$_3$, 6H, s), 3.84 (2×NCH$_3$, 6H, s), 6.89 (2×py-CH, 2H, d, J=2 Hz), 6.94 (2×py-CH, 2H, d, J=2 Hz), 7.05 (2×py-CH, 2H, d, J=2 Hz, 7.15 (2×py-CH, 2H, d, J=2 Hz), 7.19 (2×py-CH, 2H, d, J=2 Hz), 7.23 (2×py-CH, 2H, d, J=2 Hz), 8.25 (2×CONHCH$_2$, 4H, tr, J=6 Hz), 8.72 [2×C(NH$_2$)$_2$Cl, 4H, s], 9.02 [2×C(NH$_2$)$_2$Cl, 4H, s], 9.83 (2×py-NHCO, 2H, s), 9.92 (4×py-NHCO, 4H, s); MS (FAB), 1270 (M-2×Cl-H, 0.10).

EXAMPLE 17

Bis-distamycin (Compound 29)

A solution of benzene-1,4-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 77% yield. m.p., >300° C.; $^1$H-NMR, 2.63 [2×C $\underline{H}_2$C(NH$_2$)$_2$Cl, 4H, tr, J=6 Hz], 3.50 (2×CONHC$\underline{H}_2$4H, tr, J=6 Hz), 3.82 (2×NCH$_3$6H, s), 3.86 (2×NCH$_3$, 6H, s), 3.90 (2×NCH$_3$, 6H, s), 6.97 (2×py-CH, 2H, d, J=1.6 Hz), 7.09 (2×py-CH, 2H, d, J=1.6 Hz), 7.15 (2×py-CH, 2H, d, J=1.6 Hz), 7.20 (2×py-CH, 2H, d, J=1.6 Hz), 7.26 (2×y-CH, 2H, d, J=1.6 Hz), 7.38 (2×py-CH, 2H, d, J=1.6 Hz), 8.10 (aromatic-CH, 4H, s), 8.25 (2×CONHCH$_2$, 2H, tr, J=6 Hz), 8.65 [2×C(NH$_2$)$_2$Cl, 4H, s], 9.01 [2×C(NH$_2$)$_2$Cl, 4H, s], 9.95 (2×py-NHCO, 2H, s), 10.03 (2×py-NHCO, 2H, s), 10.57 (2×py-NHCO, 2H, s); (CD$_3$OD), 2.71 [2×C$\underline{H}_2$C(NH$_2$)$_2$Cl, 4H, tr, J= 7 Hz], 3.65 (2×CONHC$\underline{H}_2$, 4H, tr, J=7 Hz), 3.87 (2×NCH$_3$, 6H, s), 3.91 (2×NCH$_3$6H, s), 3.95 (2×NCH$_3$, 6H, s), 6.90 (2×ph-CH, 2H, d, J=1.8 Hz), 6.98 (2×py-CH, 2H, d, J=1.8 Hz), 7.07 (2×py-CH, 2H, d, J=1.8 Hz), 7.16 (2×py-Ch, 2H, d, J=1.8 Hz), 7.20 (2×py-CH, 2H, d, J=1.8 Hz), 7.34 (2×py-CH, 2H, d, J=1.8 Hz), 8.04 (aromatic-CH, 4H, s); MS (FAB), 1037 (M-2×Cl-H, 0.05).

EXAMPLE 18

Bis-distamycin (Compound 30)

A solution of benzene-1,3-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 ml of THF was added to the reaction solution. The resulting mixture was stirred overnight. The solvent was evaporated and the crude product was recrystallized from methanol and ether. The final product was obtained as a light yellow solid in 68% yield. m.p., 240° C.; $^1$H-NMR, 2.61 [2×C $\underline{H}_2$C(NH$_2$)$_2$Cl, 4H, tr, J=6 Hz], 3.48 (2×CONHC$\underline{H}_2$, 4H, tr, J=6 Hz), 3.80 (2×NCH$_3$, 6H, s), 3.86 (2×NCH$_3$, 6H, s), 3.91 (2×NCH$_3$, 6H, s), 6.97 (2×py-CH, 2H, d, J=1.6 Hz), 7.09 (2×py-CH, 2H, d, J=1.6 Hz), 7.16 (2×py-CH, 2H, d, J=1.6 Hz), 7.20 (2×py-CH, 2H, d, J=1.6 Hz), 7.25 (2×py-CH, 2H, d, J=1.6 Hz), 7.38 (2×py-CH, 2H, d, J=1.6 Hz), 7.66 (5-aromatic-CH, 1H, tr, J=7.5 Hz), 8.10 (4,6-aromatic-CH, 2H, d, J$^1$=8 Hz); 8.21 (2-aromatic-CH, 1H, br, s); 8.21 (2×CONHCH$_2$, 2H, br, s), 8.58 [2×C$\underline{Y}_2$C(NH$_2$)$_2$Cl, 4H, tr, J=7 Hz], 3.64 (2×CONHCH$_2$, 4H, tr, J=7 Hz), 3.88 (2×NCH$_3$, 6H, s), 3.90 (2×NCH$_3$, 6H, s), 3.94 (2×NCH$_3$, 6H, s), 6.89 (2×py-CH, 2H, d, J=1.8 Hz), 6.97 (2×ph-CH, 2H, d, J=1.8 Hz), 7.07 (2×py-CH, 2H, d, J=1.8 Hz), 7.20 (2×py-CH, 2H, d, J=1.8 Hz), 7.33 (2×py-CH, J=1.8 Hz), 7.65 (5-aromatic-CH, 1H, tr, J=7.5 Hz), 8.08 (4,6-aromatic-CH, 2H, d,d, J$_1$=7.5 Hz, J$_2$=2 Hz), 8.47 (2-aromatic-CH, 1H, br, tr, J=2 Hz); MS (FAB), 1037 (−2×Cl-H, 0.43).

EXAMPLE 19

Bis-distamycin (Compound 31)

A solution of benzene-1,2-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 83% yield. m.p., 245° C.; $^1$H-NMR (CD$_3$OD), 2.71 [2×CH$_2$C(NH$_2$)$_2$Cl, 4H, tr, J=6 Hz], 3.63 (2×CONHCH$_2$, 4H, tr, J=6 Hz), 3.87 (2×NCH$_3$, 6H, s),3.88 (2×NCH$_3$, 6H, s), 3.90 (2×NCH$_3$, 6H, s), 6.89 (2×py-CH, 2H, d, J=2 Hz), 6.91 (2×py-Ch, 2H, d, J=2 Hz), 6.97 (2×py-CH, 2H, 2H, d, J=2 Hz), 7.15 (2×py-CH, 2H, d, J=2 Hz), 7.18 (2×py-CH, 2H, d, J=2 Hz), (2×py-CH, 2H, d, J=2 Hz), 7.60 (2×m-aromatic-CH, 2H, q, J=3 Hz), 7.68 (2×o-aromatic-CH, 2H, q, J=3 Hz); MS (FAB), 1037 (m-2×Cl-H, 0.65).

EXAMPLE 20

Bis-distamycin (Compound 32)

A solution of 3,5-pyridine dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid m.p. 250° C. in 88% yield. m.p., 250° C.; $^1$H-NMR, 2.52 [2×CH$_2$C(NH$_2$)$_2$Cl, 4H, m], 3.48 (2×CONHCH$_2$, 4H, m), 3.81 (2×NCH$_3$, 6H, s), 3.85 (2×NCH$_3$, 6H, s), 3.88 (2×NCH$_3$, 6H, s), 3.90 (2×NCH$_3$, 6H, s), 6.96 (2×py-CH, 2H, m), 7.09 (2×py-CH, 2H, d, J=2 Hz), 7.17 (py-CH, 1H, d, J=2 Hz), 7.19 (2×py-CH, 2H, d, J=2 Hz), 7.25 (2×py-CH, 2H, d, J=2 Hz), 7.29 (py-CH, 1H, m), 7.40 (py-CH, 1H, m), 7.42 (py-CH, 1H, m), 8.23 (2×CONHCH$_2$, 2H, m), 8.25 (3-py-CH, 1H, d, J=8 Hz), 8, 54 (4-py-CH, 1H, m), 8.64 [2×C(NH$_2$)$_2$Cl, 4H, s], 8.99 [2×C(NH$_2$)$_2$Cl, 4H, s], 9.20 (96-py-CH, 1H, m), 9.95 (2×py-NHCO, 2H, s), 10.04 (2×py-NHCO, 2H, s), 10.94 (py-NHCO, 1H,s), 11.00 (py-NHCO, 1H, s); (CD$_3$OD), 2.72 [2×CH$_2$C(NH$_2$)$_2$Cl, 4H, tr, J=6 Hz], 3.65 (2×CONHCH$_2$, 4H, tr, J=6 Hz), 3.87 (2×NCH$_3$, 6H, s), 3.91 (2×NCH$_3$6H, s), 3.94 (NCH$_3$, 3H, s), 3.954 (NCH$_3$, 3H, s), 6.90 (2×py-CH, 2H, d, J=2 Hz), 6.98 (2×py-CH, 2H, d, J=2 Hz), 7.07 (py-CH, 1H, d, J=2 Hz), 7.10 (py-CH, 1H, d, J=2 Hz), 7.15 (2×py-CH, 2H, d, J=2 Hz) 7.20 (2×py-CH, 2H, d, J=2 Hz), 7.34 (py-CH, 1H, d, J=2 Hz), 7.41 (py-CH, 1H, d, J=2 Hz), 8.27 (3-py-CH, 1H, d, J=8 Hz), 8.44 (4-py-CH, 1H, m), 9.17 (6-py-CH, 1H, m); MS (FAB), 1038 (M-2×Cl-H, 0.03).

EXAMPLE 21

Bis-distamycin (Compound 33)

A solution of pyridine-3,6-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 74% yield. m.p., 260° C.; $^1$H-NMR, 2.62 [2×CH$_2$C(NH$_2$)$_2$Cl, 4H, tr, J=6 Hz], 3.50 (2×CONHCH$_2$4H, q, J=6 Hz), 3.81 (2×NCH$_3$, 6H, s), 3.85 (2×NCH$_3$, 6H, s), 3.90 (2×NCH$_3$, 6H, s), 6.96 (2×xpy-CH, 2H, d, J=2 Hz), 7.08 (2×py-CH 2H, d, J=2 Hz, 7.16 (2×py-CH, 2H, d, J=2 Hz), 7.18 (2×py-CH, 2H, d, J=2 Hz), 7.26 (2×py-CH, 2H, d, J=2 Hz), 7.39 (2×py-CH, 2H, d, J=2 Hz), 8.23 (2×CONHCH$_2$, 2H, tr, J=6 Hz), 8.59 [2×C(NH$_2$)$_2$Cl, 4H, s], 8.87 (4-py-CH, 1H, br,s), 8.98 [2×C(NH$_2$)$_2$Cl, 4H, s], 9.24 (2,6-py-CH, 2H, d, J=2 Hz), 9.94 (2×py-NHCO, 2H, s), 10.05 (2×py-NHCO, 2H, s), 10.83 (2×py-NHCO, 2H, s); (CD$_3$OD), 2.71 [2×CH$_2$C(NH$_2$)$_2$Cl, 4H, tr, J=6 Hz], 3.64 (2×CONHCH$_2$, 4H, tr, J=6 Hz), 3.87 (2×NCH$_3$, 6H, s), 3.99 (2×NCH$_3$, 6H, s), 4.02 (2×NCH$_3$, 6H, s), 6.88 (2×py-CH, 2H, s), 6.96 (2×py-CH, s), 7.07 (2×py-CH, 2H, s), 7.15 (2×py-CH, 2H, s), 7.19 (2×py-CH, 2H, s), 7.35 (2×py-CH, 2H, s), 8.82 (4-py-CH, 1H, s), 9.17 (2,5-py-CH, 2H, s); MS (FAB), (M-2×CL-H, 0.15).

EXAMPLE 22

Bis-distamycin (Compound 34)

A solution of pyridine-2,6-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 54% yield. m.p., >260° C; $^1$H-NMR, 2.62 [2×CH$_2$(NH$_2$)$_2$Cl, 4H, tr, J=6 Hz], 3.50 (2×CONHCH$_2$, 4H, m), 3.82 (2×NCH$_3$, 6H, s), 3.86 (2×NCH$_3$, 6H, s), 3.90 (2×NCH$_3$, 6H, s), 6.97 (2×py-CH, 2H, d, J=2 Hz), 7.08 (2×py-CH, 2H, d, J=2 Hz), 7.15 (2×py-CH, 2H, d, J=2 Hz), 7.18 (2×py-CH, 2H, d, J=2 Hz), 7.18 (2×py-CH, 2H, d, J=2 Hz), 7.25 (2×py-CH, 2H, d, J=2 Hz), 7.39 (2×py-CH, 2H, d, J=2 Hz), 8.23 (2×CONHCH$_2$, 2H, tr, J=6 Hz, 8.56 [2×C(NH$_2$)$_2$Cl, 4H, s], 8.85 (4-py-CH, 1H, tr, J=2 Hz), 8.96 [2×C(NH$_2$)$_2$Cl, 4H, s], 9.24 (3,5-py-CH, 2H, d, J=2 Hz), 9.94 (2×py-NHCO, 2H, s), 10.04 (2×py-NHCO, 2H, s), 10.81 (2×py-NHCO, 2H, s); MS (FAB), 1038 (M-2×Cl-H, 0.25).

EXAMPLE 23

Bis-distamycin (Compound 35)

A solution of trans-1,2-cyclobutane-dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 µL, 0.09 mmol) in 3 mL of dimethylformamide cooled to 0° C. After 10 min, a solution of Hunig's base (16 µL, 0.09 mmol)

in 3 mL of THF was added to the reaction solution. The resulting mixture was stirred overnight. The solvent was evaporated and the crude product was recrystallized from methanol and ether. The final product was obtained as a light yellow solid in 78% yield. m.p., >230° C.; $^1$H-NMR, 2.05 (3,4-cyclobutane-$CH_2$, 4H, m), 2.60 ($2\times CH_2C(NH_2)_2Cl$, 4H, tr, J=6 Hz], 3.38 (1,2-cyclobutane-CH, 2H, m), 3.49 ($2\times CONHCH_2$, 4H, tr, J=6 Hz), 3.79 ($2\times NCH_3$, 6H, s), 3.84 ($2\times NCH_3$, 6H, s), 3.85 ($2\times NCH_3$, 6H, s), 6.88 ($2\times$py-CH, 2H, d, J=1.8 Hz), 6.97 ($2\times$py-CH, 2H, d, J=1.8 Hz), 7.05 ($2\times$py-CH, 2H, d, J=1.8 Hz), 7.17 ($2\times$py-CH, 2H, d, J=1.8 Hz), 7.21 ($2\times$py-CH, 2H, d, J=1.8 Hz), 7.23 ($2\times$py-CH, 2H, d, J=1.8 Hz), 8.22 ($2\times CONHCH_2$, 2H, tr, J=6 Hz), 8.55 [$2\times c(NH_2)_2Cl$, 4H, s], 8.96 [$2\times C(NH_2)_2Cl$, 4H, s], 9.88 ($2\times$py-NHCO, 2H, s), 9.94 ($4\times$py-NHCO, 2H, s); ($CD_3OD$), 2.20 (3,4-cyclobutane-$CH_2$, 4H, m), 2.71 ($2\times CH_2$, 4H, tr, J=7 Hz), 3.49 (1,2-cyclobutane-CH, 2H, m), 3.64 [$2\times CH_2C(NH_2)_2Cl$, 4H, tr, J=7 Hz), 3.87 ($2\times NCH_3$, 6H, s), 3.89 ($2\times NCH_3$, 6H, s), 3.90 ($2\times NCH_3$, 6H, s), 6.84 ($2\times$py-CH, 2H, d, J=2 Hz), 6.89 ($2\times$py-CH, 2H, d, J=2 Hz), 6.95 ($2\times$py-CH, 2H, d, J=2 Hz), 7.15 ($2\times$py-CH, 2H, d, J=2 Hz), 7.18 ($2\times$py-CH, 2H, d, J=2 Hz), 7.20 ($2\times$py-CH, 2H, d, J=2 Hz); MS (FAB), 1015 (M-$2\times$Cl-H, 1.06).

EXAMPLE 24

Bis-distamycin (Compound 36)

A solution of maleic-dichloride (9.28 mg, 0.046 mmol) in 5 mL of tetrahydrofuran was added to a solution of deformyl distamycin (48 mg, 0.09 mmol) and dissiopropylethylamine (Hunig's base, 16 μL, 0.09 mmol) in 3 mL of dimethylformamide cooled to 0° C. After 10 min, a solution of Hunig's base (16 μL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 33% yield. m.p., >255° C.; $^1$H-NMR, 2.61 [$2\times CH_2C(NH_2)_2Cl$, 4H, tr, J=6 Hz], 3.50 ($2\times CONHCH_2$, 4H, q, J=6 Hz), 3.82 ($2\times NCH_3$, 6H, s), 3.85 ($2\times NCH_3$ 6H, s), 3.87 ($2\times NCH_3$ 6H, s),6.97 ($2\times$py-CH, 2H, tr, J=2 Hz), 7.07 ($2\times$py-CH, 2H, d, J=2 Hz), 7.10 (—CH=CH—, 2H, s), 7.18 ($2\times$py-CH, 2H, s), 7.24 ($2\times$py-CH, 2H, d, J=2 Hz), 7.35 ($2\times$py-CH, 2H, d, J =2 Hz), 8.23 ($2\times CONHCH_2$, 2H, tr, J=6 Hz), 8.66 [$2\times C(NH_2)_2Cl$, 4H, s], 8.94 [$2\times C(NH_2)_2Cl$, 4H, s], 9.93 ($2\times$pyNHCO, 2H, s), 9.99 ($2\times$py-NHCO, 2H, s), 10.54 ($2\times$py-NHCO, 2H, s),, ($CD_3OD$), 2.72 [$2\times CH_2C(NH_2)_2Cl$, 4H, tr, J=6 Hz], 3.65 ($2\times CONHCH_2$, 4H, tr, J=6 Hz), 3.88 ($2\times NCH_3$, 6H, s), 3.90 ($2\times NCH_3$, 6H, s), 3.92 ($2\times NCH_3$, 6H, s), 6.91 ($2\times$py-CH, 2H, tr, J=2 Hz), 6.98 ($2\times$py-CH, 2H, d, J=2 Hz), 7.09 (—CH=CH—, 2H, s), 7.16 ($2\times$py-CH, 2H, d, J=2 Hz), 7.19 ($2\times$py-CH, 2H, d, J=2 Hz), 7.33 ($2\times$py-CH, 2H, d, J=2 Hz); MS (FAB), 987 (M-$2\times$Cl-H, 0.27).

EXAMPLE 25

Bis-distamycin (Compound 37)

A solution of fumaroyl-dichloride (9.28 mg, 0.046 mmol) in 5 mL of tetrahydrofuran was added to a solution of deformyl distamycin (48 mg, 0.09 mmol) and dissiopropylethylamine (Hunig's base, 16 μL, 0.09 mmol) in 3 mL of dimethylformamide cooled to 0° C. After 10 min, a solution of Hunig's base (16 μL, 0.09 mmol) in 3 mL of THF was added to the reaction solution. The resulting mixture was stirred overnight. The solvent evaporated and the crude product was obtained as a light yellow solid in 67% yield. m.p., >280° C.; $^1$H-NMR, 2.61 [$2\times CH_2C(NH_2)_2Cl$, 4H, tr, J=6 Hz], 3.48 ($2\times CONHCH_2$, 4H, tr, J=6 Hz); 3.80 ($2\times NCH_3$, 6H, s), 3.84 ($2\times NCH_3$, 6H, s), 3.86 ($2\times NCH_3$, 6H, s), 6.35 (—CH=CH—, 2H, s), 6.84–7.84 ($12\times$py-CH, 12H, m), 8.24 ($2\times CONHCH_2$, 2H, tr, J=6 Hz), 8.58–9.50 [$2\times C(NH_2)_2Cl$, 8H, br, s], 9.93 ($2\times$py-NHCO, 2H, s), 9.97 ($2\times$py-NHCO, 2H, s), 9.98 ($2\times$py-NHCO, 2H, s); ($CD_3OD$), 2.66 [$2\times CH_2C(NH_2)_2Cl$, 4H, tr, J=6 Hz], 3.58 ($2\times CONHCH_2$, 4H, tr, J=6 Hz), 3.79 ($2\times NCH_3$, 6H, s), 3.82 ($2\times NCH_3$, 6H, s), 3.84 ($2\times NCH_3$, 6H, s), 6.26 (—CH=CH—, 2H, s), 6.83 ($2\times$py-CH, 2H, d, J=2 Hz), 6.87 ($2\times$py-CH, 2H, d, J=2 Hz), 6.91 ($2\times$py-CH, 2H, d, J=2 Hz), 7.13 ($2\times$py-CH, 2H, d, J=2 Hz), 7.17 ($2\times$py-CH, 2H, d, J=2 Hz), 7.27 ($2\times$py-CH, 2H, d, J=2 Hz); MS (FAB), no M+1 peak.

EXAMPLE 26

Bis-distamycin 35 (Compound 38)

A solution of trans-5,6-bicyclo[2,2,1]-hept-2-ene dicarbonyl dichloride (9.28 mg, 0.046 mmol) in 5 mL of tetrahydrofuran was added to a solution of deformyl distamycin (48 mg, 0.09 mmol) and dissiopropylethylamine (Hunig's base, 16 μL, 0.09 mmol) in 3 mL of dimethylformamide cooled to 0° C. After 10 min, a solution of Hunig's base (16 μL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 53% yield. m.p., 260° C.; $^1$H-NMR, 1.31 (7-bicyclohept, 1H, s), 1.86 (7-bicyclohept, 1H, d, J=7 Hz), 2.76 (5-endo-bicyclohept, 1H, d, J=8 Hz), 2.93 (4-bicyclohept, 1H, s), 3.35 (1-bicyclohept, 1H, s), 3.50 (6-exo-cyclohept, 1H, s), 3.50 [$2\times CH_2C(NH_2)_2Cl$, 4H, m], 3.81 ($3\times NCH_3$, 9H, s), 3.85 ($3\times NCH_3$, 9H, s), 5.98 (3-bicyclohept, 1H, d,d, J =2.5 Hz), 6.30 (2-bicyclohept, 1H, d,d, J=2.5 Hz), 6.86 (py-CH, 1H, d, J=2 Hz), 6.91 (py-CH, 1H, d, J=2 Hz), 6.97 ($2\times$py-CH, 2H, d, J=2 Hz), 7.06 ($2\times$py-CH, 2H, d, J =2 Hz), 7.13 (py-CH, 1H, d, J=2 Hz), 7.18 ($2\times$py-CH, 2H, d, J=2 Hz), 7.19 (py-CH, 1H, d, J=2 Hz), 7.23 ($2\times$py-CH, 2H, tr, J=2 Hz), 8.24 ($2\times CONHCH_2$, 2H, m), 8.57 [$2\times C(NH_2)_2Cl$, 4H, m], 8.97 [$23\times C(NH_2)_2Cl$, 4H, m], 9.88 (py-NHCO, 1H, m), 9.92 ($4\times$py-CH, 4H, m), 10.11 (Ipy-NHCO, 1H, m); ($CD_3OD$), 1.47 (7-bicyclohept, 1H, d, J=8 Hz), 1.94 (7-bicyclohept, 1H, d, J=8 Hz), 2.71 [$2\times CH_2C(NH_2)_2Cl$, 4H, d, J=6 Hz), 2.77 (5-endo-bicyclohept, 1H, d, J=4 Hz), 3.04 (4-bicyclohept, 1H, s), 3.47 (6-exo-bicyclohept, 1H,), 3.64 ($2\times CONHCH_2$, 4H, tr, J=6 Hz), 3.87 ($2\times NCH_3$, 9H, s), 3.89 ($NCH_3$, 3H, s), 3.90 ($2\times NCH_3$, 6H, s), 6.08 (3-bicyclohept, 1H, d, J=2.5 Hz), 6.37 (2-bicyclohept, 1H, d, J=2.5 Hz), 6.82 (py-CH, 1H, d, J=2 Hz), 6.83 (py-CH, 1H, d, J=2 Hz), 6.89 ($2\times$py-CH, 2H, d, J=2 Hz), 6.95 ($2\times$py-CH, 2H, d, J=2 Hz), 7.11 (py-CH, 1H, d, J=2 Hz), 7.14 ($2\times$py-CH, 2H, d, J=2 Hz), 7.17 ($3\times$py-CH, 3H, tr, J=2 Hz); MS (FAB), 1053 (M-$2\times$Cl-H, 0.21).

EXAMPLE 27

Bis-Lexitropsin (Compound 39)

A solution of maleic-dichloride (9.28 mg, 0.046 mmol) in 5 mL of tetrahydrofuran was added to a solution of 3-[1-methyl-4-(4-amino-1-methylimidazole-2-carboxamido) imidazole-2-carboxamido]propionamidine hydrochloride (48 mg, 0.09 mmol) and dissiopropylethylamine (Hunig's base, 16 μL, 0.09 mmol) in 3 mL of dimethylformamide cooled to 0° C. After 10 min, a solution of Hunig's base (16 μL, 0.09 mmol) in 3 mL of THF was added to the reaction solution. The resulting mixture was stirred overnight. The solvent was evaporated and the crude product was recrystallized from methanol and ether. The final product was obtained as a light yellow solid in 73% yield. m.p., >250° C.; $^1$H-NMR, 1.86 (2×CH$_2$CH$_2$CH$_2$, 4H, q, J=8 Hz), 3.00 [2×CH$_2$N(CH$_3$)$_2$, 4H, tr, J=8 Hz], 3.30 (2×CONHCH$_2$, 4H, m), 3.96 (2×NCH$_3$, 6H, s), 4.02 (2×NCH$_3$, 6H, s), 7.28 (—CH═CH—, 2H, s), 7.54 (2×im-CH, 2H, s), 7.67 (2×im-CH, 2H, s), 8.52 (2×CONHCH$_2$, 2H, tr, J=6 Hz), 9.43 (2×py-NHCO, 2H, s), 11.01 (2×py-NHCO, 2H, s); MS (FAB), 777 (M-2×Cl-H, 3.11).

Other compounds shown in Table I were similarly prepared and their analytical and physical data are summarized therein.

EXAMPLE 28

Drug-DNA binding constants of the compounds of the present invention were estimated. To 2 mL of Tris-EDTA buffer, pH 8, containing 1.3 μM ethidium bromide, calf thymus DNA was added to give a final concentration of 1.35 μM. The fluorescence was measured after equilibration for a few minutes, using a Turner model 430 spectrofluorometer (Turner Amsco Instruments, Carpinteria, Calif.) equipped with a 150 W xenon lamp, at an excitation wavelength of 525 nm and an emission wavelength of 600 nm. Aliquots of concentrated drug solutions were added and the fluorescence measured. Controls were performed to show that the drugs themselves did not interfere with the fluorescence measurements at the levels employed. From a plot of the decreased fluorescence of the ethidium-DNA complex with increase dose of drug, the concentration of drug needed to reduce the fluorescence by 50% was determined and used to calculate a relative binding constant for the drug, given the binding constant of ethidium to be $10^7$ M$^{-1}$ under similar conditions.

The results of binding tests are shown in Table II and in Table III.

EXAMPLE 29

Compounds of the present invention were tested for anti-Moloney murine leukemia virus (MLV). The method utilized was adapted from Rowe et al (1970) and Lin et al (1987).

The following materials were utilized in the method:

Retroviruses; rauscher—ATCC 998 moloney LT(V)—ATCC 190 Leukosis-sarcoma complex—ATCC 245 cells; SC-1—ATCC CRL 1404 XC—ATCC CCL 165 minimum essential medium (eagle) with Hanks Bss supplemented with 10% fetal bovine serum, 100 1U ml$^{-1}$ penicillin G, 100 ugml$^{-1}$ streptomycin, 2.5 ugml$^{-1}$ amphotericin B and non-essential amino acids (Sigma M2025).

Dulbecco's modified eagles medium, supplemented with 10% fetal bovine with 5% fetal bovine serum, 100 10ml$^{-1}$ penicillin G, 100 ugml$^{-1}$ streptomycin and 2.5 ugml$^{-1}$ amphotericin B.

minimum essential medium (eagle) with earles salt supplemented with 5% fetal bovine serum, 100 10 ml$^{-1}$ penicillin G, 100 ugml$^{-1}$ streptomycin and non-essential aminoacids (Sigma M2025).

phosphate buffered saline.

crystal violet dye.

24 well plates.

compounds dissolved in DMSO (or water) to 2–20 ugml$^{-1}$ then further diluted in 5% FBS-MEM.

Stock cell cultures were prepared in the 10% FBS-Dulbecco. To prepare 24 well plates for experiments, 0.8 ml of 3.5×10$^4$ SC$^1$ cells ml$^{-1}$ were added to each well one day in advance. This was using the 5% FBS-MEM. 0.1 ml of each compound dilution, in triplicate, was added to a well in the plate. 0.1 ml of 20–40 p.f.u. of moloney virus was added to each well of the plate. Those plates were shaken on a mechanical shaker at 0, 30 and 60 minutes. They were incubated for 5 days at 37° C. in a 5% Co$_2$ incubator. The medium was removed and plates were subjected to ultraviolet light (175 W cm$^2$ at surface) for three minutes.

0.8 ml of 2×10$^5$ XC cells ml$^{-1}$ were added to each well using the 10% FBS-Hanks mem. The plates were incubated at 37° C., 5% CO$_2$ for 4 days, but the medium was replaced after 2 days. The medium was removed, the wells were washed with pbs and 0.25 ml of 0.05% crystal violet was added to each well for 2 hours. The plates were washed, dried and the plaques counted.

MIC$_{50}$ values were calculated using the formula—

$$\frac{\% \text{ inhibition greater than } 50\% - 50\%}{\% \text{ inhibition greater than } 50\% - \% \text{ inhibition less than } 50\%}$$

to give the interpolative values between two dilutions.

The results of the test are shown in Tables IV and V and demonstrate comparative anti-MLV activity between compounds of the present invention and AZT and DDC.

EXAMPLE 30

Compounds of the present invention were tested for anti-HIV activity by the National Cancer Institute (NIH, Bethesda). The procedure used by the National Cancer Institute is described in Weislow, O. W. et al, *J. Natl. Cancer Inst.*, Vol. 81, pages 577–586 (1989). NCI uses this procedure to test for agents active against Human Immunodeficiency Virus (HIV) and is designed to detect agents acting at any stage of the virus reproductive cycle. The assay basically involves the killing of T4 lymphocytes by HIV. Small amounts of HIV are added to cells, and a complete cycle of virus reproduction is necessary to obtain the required cell killing. Agents that interact with virions, cells, or virus gene-products to interfere with viral activities will protect cells from cytolysis. The system is automated in several features to accommodate large numbers of candidate agents and is generally designed to detect anti-HIV activity. However, compounds that degenerate or are rapidly metabolized in the culture conditions may not show activity in this screen. All tests are compared with at least one positive (e.g., AZT-treated) control done at the same time under identical conditions. The procedure is set forth below:

1. Candidate agent is dissolved in dimethyl sulfoxide (unless otherwise instructed) then diluted 1:100 in cell culture medium before preparing serial half-log$_{10}$ dilutions. T4 lymphocytes (CEM cell line) are added and after a brief interval HIV-1 is added, resulting in a 1:200 final dilution of the compound. Uninfected cells with the compound serve as a toxicity control, and infected and uninfected cells without the compound serve as basic controls.

2. Cultures are incubated at 37° in a 5% carbon dioxide atmosphere for 6 days.

3. The tetrazolium salt, XTT, is added to all wells, and cultures are incubated to allow formzan color development by viable cells.

4. Individual wells are analyzed spectrophotometrically to quantitate formazan production, and in addition are viewed microscopically for detection of viable cells and confirmation of protective activity.

5. Drug-treated virus-infected cells are compared with drug-tested noninfected cells and with other appropriate controls (untreated infected and untreated noninfected cells, drug-containing wells without cells, etc.) on the same plate.

6. Data are reviewed in comparison with other tests done at the same time and a determination about activity is made.

The test results for five of the active compounds are set forth in the FIGS. 2–6 and the corresponding Tables VI–X below and test results of the compounds of the present invention are compilated in Table XI.

TABLE I

Analytical and physical data on linked netropsins and their precursors

| Comp. | Yield(5) | m.p.[a] | Formula | Analysis |
|---|---|---|---|---|
| 15 | 85 | 210° | $C_{46}H_{58}N_{18}O_8Cl_2$ | C, H, N, Cl |
| 16 | 76 | 210° | $C_{50}H_{60}N_{18}O_8Cl_2$ | C, H, N, Cl |
| 17 | 84 | 198–202 | $C_{52}H_{64}N_{18}O_8Cl_2$ | C, H, N, CL |
| 18 | 69 | 215 | $C_{66}H_{92}N_{18}O_8Cl_2$ | C, H, N, CL |
| 19a | 99 | 305–6° | $C_{38}H_{38}N_{12}O_6$ | C, H, N |
| 19b | 64 | 262–8° | $C_{38}H_{46}N_{14}O_6Cl_2$ | C, H, N, Cl |
| 20a | 95 | 278–82° | $C_{38}H_{38}N_{12}O_6$ | C, H, N |
| 20b | 78 | 248–50° | $C_{38}H_{46}N_{14}O_6Cl_2$ | C, H, N, Cl |
| 21a | 84.7 | 289–90° | $C_{34}H_{36}N_{12}OL_6$ | C, H, N |
| 21b | 58 | 295° | $C_{34}H_{44}N_{14}O_6Cl_2$ | C, H, N, Cl |
| 22a | 56.5 | 25_14 2° | $C_{34}H_{36}N_{12}O_6$ | C, H, N |
| 22b | 85 | 217° | $C_{34}H_{44}N_{14}O_6Cl_2$ | C, H, N, Cl |
| 23a | 88.6 | 312° (dec) | $C_{35}H_{38}N_{12}O_6$ | C, H, N |
| 23b | 68.5 | 210° (softens) | $C_{35}H_{46}N_{14}O_6Cl_2$ | C, H, N, Cl |
| 24a | 59 | 175° | $C_{35}H_{38}N_{12}O_6$ | C, H, N |
| 24b | 70.6 | 204° (softens) | $C_{35}H_{46}N_{14}O_6Cl_2$ | C, H, N, Cl |
| 25a | 69 | 172° (softens) | $C_{36}H_{40}N_{12}O_6$ | C, H, N |
| 25b | 77 | 238° (softens) | $C_{36}H_{48}N_{14}O_6CL_2$ | C, H, N, Cl |
| 26a | 70 | 165–8° | $C_{37}H_{42}N_{12}O_6$ | C, H, N |
| 26b | 46 | 231° | $C_{37}H_{50}N_{14}O_6Cl_2$ | C, H, N, Cl |
| 27a | 82.6 | 189° | $C_{38}H_{44}N_{12}O_6$ | C, H, N |
| 27b | 61 | 201° (softens) | $C_{38}H_{52}N_{14}O_6Cl_2$ | C, H, N, Cl |
| 28a | 54 | 175° | $C_{38}H_{44}N_{12}O_6$ | C, H, N |
| 28b | 23 | 198° | $C_{38}H_{52}N_{14}O_6Cl_2$ | C, H, N, Cl |
| 29 | 77 | >300 | $C_{50}H_{58}N_{18}O_8Cl_2$ | C, H, N, CL |
| 30 | 68 | 240 | $C_{50}H_{58}N_{18}O_8Cl_2$ | C, H, N, CL |
| 31 | 83 | 245 | $C_{50}H_{58}N_{18}O_8Cl_2$ | C, H, N, CL |
| 32 | 88 | 250 | $C_{49}H_{57}N_{19}O_8Cl_2$ | C, H, N, CL |
| 33 | 74 | 260 | $C_{49}H_{57}N_{19}O_8Cl_2$ | C, H, N, CL |
| 34 | 54 | 260 | $C_{49}H_{57}N_{19}O_8Cl_2$ | C, H, N, CL |
| 35 | 78 | 230 | $C_{48}H_{60}N_{18}O_8Cl_2$ | C, H, N, CL |
| 36 | 33 | 255 | $C_{46}H_{56}N_{18}O_8Cl_2$ | C, H, N, CL |
| 37 | 67 | 280 | $C_{46}H_{56}N_{18}O_8Cl_2$ | C, H, N, CL |
| 38 | 53 | 260 | $C_{51}H_{62}N_{18}O_8Cl_3$ | C, H, N, CL |
| 39 | 73 | 250 | $C_{34}H_{50}N_{16}O_6Cl_2$ | C, H, N, CL |

[a]Uncorrected.
[b]All compounds gave satisfactory elemental analyses within 0.4% of the calculated values and exhibited $^1$H—NMR, IR and MS data consistent with the structures.

TABLE II

Relative binding constants for natural and linked oligopeptides $R_1CO(CH_2)_nCO$—$R_1$ to calf thymus DNA determined by ethidium displacement assay.[a]

| Compound | n[b] | DNA Binding Constant ($M^{-1}$) |
|---|---|---|
| 1 | — | $1.9 \times 10^7$ |
| 2 | — | $0.8 \times 10^7$ |
| 3 | 0 | $5.6 \times 10^7$ |
| 4 | 1 | $3.6 \times 10^7$ |
| 5 | 2 | $7.2 \times 10^7$ |
| 8 | 5 | $1.2 \times 10^7$ |
| 9 | 6 | $2.5 \times 10^7$ |
| 10 | 7 | $0.9 \times 10^7$ |
| 11 | 8 | $1.7 \times 10^7$ |
| 12 | 9 | $1.9 \times 10^7$ |
| 13 | 10 | $2.2 \times 10^7$ |

[a]Based on a binding constant of ethidium of $10^7 M^{-1}$ under similar conditions of temperature, pH and ionic strength. Binding constant values represent the average of repeat measurements.
[b]Number of $CH_2$ units in the linker in $R_1$—$CO(CH_2)_nCO$—$R_1$.

TABLE III

Relative binding constants for cis and trans bis-netropsins to poly(dA–dT) determined by the ethidium displacement assay.[a]

| Compound | $K_{app}(M^{-1})$ |
|---|---|
| 1 | $9.4 \times 10^7$ |
| 2 | $6.3 \times 10^7$ |
| 19b | $4.3 \times 10^7$ |
| 20b | $4.9 \times 10^7$ |
| 21b | $4.9 \times 10^7$ |
| 22b | $3.8 \times 10^7$ |
| 23b | $5.3 \times 10^7$ |
| 24b | $4.4 \times 10^7$ |
| 25b | $5.6 \times 10^7$ |
| 26b | $3.1 \times 10^7$ |
| 27b | $4.0 \times 10^7$ |

[a]Based on a binding constant of othidium of $9.5 \times 10^6 M^{-1}$ under similar conditions of temperature, pH and ionic strength. Binding constants represent the average of repeat measurements.

TABLE IV

| Compound | Toxicity, $TD_{50}$ (ug/mL$^{-1}$) | Activity, MIC50 (ug mL$^{-1}$) | T.I., $TD_{50}$/ $MIC_{50}$ |
|---|---|---|---|
| 29 | >100.00 | 3.98 | >25.13 |
| 30 | >100.00 | >50.0 | 2.0 |
| 31 | >100.00 | 79.63 | >1.26 |
| 32 | >100.00 | 15.93 | >6.28 |
| 33 | >100.00 | >100.00 | — |
| 34 | >100.00 | 22.74 | >4.40 |
| 35 | 83.50 | >50.0 | 1.7 |
| 36 | 100.00 | 0.16 | 625.00 |
| 37 | 84.29 | 11.21 | 7.52 |
| 38 | >100.00 | 22.04 | >4.54 |
| 39 | >100.00 | >100.00 | — |
| AZT | >100.00 | 0.0014 | >7.14 × 10$^5$ |
| DDC | >100.00 | 0.74 | >135.14 |

TABLE V

Inhibition of Maloney murine loukenia (MLV) associated reverse transciptase activity by linked.

| Compound | $n^a$ | $ID_{50}^b$ (ug/mL) (average ± SD) |
|---|---|---|
| 4 | 1 | 3.90 ± 13.9 |
| 4 | 2 | 25.2 ± 11.4 |
| 8 | 5 | 72.5 ± 7.69 |
| 9 | 6 | 21.3 ± 6.1 |
| 10 | 7 | 34.2 ± 0.9 |
| 11 | 8 | 20.3 ± 9.2 |
| 12 | 9 | 10.3 ± 7.5 |
| 13 | 10 | 9.1 ± 6.7 |
| 23b | — | 7.0 ± 3.6 |
| 24b | — | 30.4 ± 19.3 |
| 25b | — | 21.8 ± 9.2 |
| 26b | — | 45.9 ± 11.3 |
| 27b | — | 29.1 ± 6.0 |
| 28b | — | 63.8 ± 41.0 |
| Aurintricarboxylic acid | | 1.42 ± 0.26 |

[a] Number of $CH_2$ groups in linker in $R_1$—$CO(CH_2)_nCO$—$R_1$.
[b] 50% inhibitory dose, measured after 120 min incubation of the reaction mixtures. [MLV: lot 804-845-8A; ($^3$H-methyl) dTTP at 10 µC; (specific activity: 30 Curies/mmol) per 250 µL of reaction mixture.)

TABLE VI

Results of the compound N,N'-di[1-methyl-2-[1-methyl-2-carboxamido(3-propionamidine)-4-pyrrole]-4-pyrrolyl] terephthalamide dihydrochloride.

| SUMMARY | | DOSE | INFECTED RESPONSE % of | UNINFECTED RESPONSE % of |
|---|---|---|---|---|
| Index | Concentration | (Molar) | Control | Control |
| IC50 (Molar) | >1.79 × 10$^{-5}$ | 5.68 × 10$^{-9}$ | 39.64 | 68.62 |
| EC50 (Molar) | 2.08 × 10$^{-6}$ | 1.79 × 10$^{-8}$ | 33.00 | 92.56 |
| TI50 (IC/EC) | >8.59 × 10$^{0}$ | 5.68 × 10$^{-8}$ | 23.70 | 94.69 |
| | | 1.79 × 10$^{-7}$ | 29.97 | 92.72 |
| | | 5.67 × 10$^{-7}$ | 28.86 | 88.21 |
| | | 1.79 × 10$^{-6}$ | 51.73 | 136.50 |
| | | 5.66 × 10$^{-6}$ | 134.54 | 164.46 |
| | | 1.79 × 10$^{-5}$ | 167.25 | 192.17 |

TABLE VII

Results of the compound N,N'-di[1-methyl-2-[1-methyl-2-carboxamido(3-propionamidine)-4-pyrrole]-4-pyrrolyl] isophthalamide dihydrochloride.

| SUMMARY | | DOSE | INFECTED RESPONSE % of | UNINFECTED RESPONSE % of |
|---|---|---|---|---|
| Index | Concentration | (Molar) | Control | Control |
| IC50 (Molar) | 2.84 × 10$^{-4}$ | 4.28 × 10$^{-7}$ | 48.47 | 116.38 |
| EC50 (Molar) | 3.55 × 10$^{-6}$ | 1.35 × 10$^{-6}$ | 29.25 | 131.95 |
| TI50 (IC/EC) | 8.00 × 10$^{+1}$ | 4.27 × 10$^{-6}$ | 64.76 | 123.64 |
| | | 1.35 × 10$^{-5}$ | 117.45 | 117.76 |
| | | 4.26 × 10$^{-5}$ | 120.68 | 123.27 |
| | | 1.34 × 10$^{-4}$ | 63.57 | 142.80 |
| | | 4.26 × 10$^{-4}$ | 0.02 | −0.29 |
| | | 1.34 × 10$^{-3}$ | 4.26 | 10.39 |

TABLE VIII

Results of the compound N,N'-di[1-methyl-2-[1-methyl-2-carboxamido(3-propionamidine)-4-pyrrole]-4-4pyrrolyl] fumaride dihydrochloride.

| SUMMARY | | DOSE | INFECTED RESPONSE % of | UNINFECTED RESPONSE % of |
|---|---|---|---|---|
| Index | Concentration | (Molar) | Control | Control |
| IC50 (Molar) | >3.30 × 10⁻⁵ | 1.05 × 10⁻⁸ | 18.00 | 83.05 |
| EC50 (Molar) | 1.67 × 10⁻⁶ | 3.32 × 10⁻⁸ | 22.96 | 67.56 |
| TI50 (IC/EC) | >1.97 × 10⁺¹ | 1.09 × 10⁻⁷ | 26.15 | 90.26 |
| | | 3.31 × 10⁻⁷ | 20.00 | 88.21 |
| | | 1.04 × 10⁻⁶ | 38.90 | 83.87 |
| | | 3.31 × 10⁻⁶ | 96.78 | 151.83 |
| | | 1.04 × 10⁻⁵ | 150.24 | 134.79 |
| | | 3.30 × 10⁻⁵ | 132.20 | 138.63 |

TABLE IX

Results of the compound N,N'-di[1-methyl-2-[1-methyl-2-carboxamido(3-propionamidine)-4-pyrrole]-4-pyrrolyl]-4-pyrrolyl]maleamide dihydrochloride.

| SUMMARY | | DOSE | INFECTED RESPONSE % of | UNINFECTED RESPONSE % of |
|---|---|---|---|---|
| Index | Concentration | (Molar) | Control | Control |
| IC50 (Molar) | 1.63 × 10⁻⁴ | 3.04 × 10⁻⁷ | 28.75 | 100.16 |
| EC50 (Molar) | 4.04 × 10⁻⁶ | 9.61 × 10⁻⁷ | 32.14 | 100.02 |
| T rft (IC/ Wy | 4.04 × 10⁺¹ | 3.03 × 10⁻⁶ | 44.03 | 103.19 |
| | | 9.59 × 10⁻⁶ | 115.19 | 112.20 |
| | | 3.03 × 10⁻⁵ | 114.32 | 112.05 |
| | | 9.54 × 10⁻⁵ | 84.02 | 94.16 |
| | | 3.02 × 10⁻⁴ | −0.29 | −0.86 |
| | | 9.57 × 10⁻⁴ | −0.14 | 5.40 |

TABLE X

Results of the compound N,N'-di[1-methyl-2-[1-methyl-2-carboxamido(3-propionamidine)-4-pyrrole]-4-pyrrolyl] trans 1,2-cyclobutaneamide dihydrochloride.

| | SUMMARY | | INFECTED RESPONSE | UNINFECTED RESPONSE |
|---|---|---|---|---|
| Index | Concentration | DOSE (Molar) | % of Control | % of Control |
| IC50 (Molar) | 1.67 × 10⁻⁴ | 2.94 × 10⁻⁷ | 42.92 | 90.95 |
| EC50 (Molar) | 1.39 × 10⁻⁶ | 9.29 × 10⁻⁷ | 59.07 | 102.41 |
| TI50 (IC/EC) | 1.20 × 10⁺² | 2.93 × 10⁻⁶ | 77.00 | 116.36 |
| | | 9.38 × 10⁻⁶ | 80.26 | 145.18 |
| | | 2.93 × 10⁻⁵ | 110.05 | 174.62 |
| | | 9.27 × 10⁻⁵ | 90.52 | 101.95 |
| | | 2.92 × 10⁻⁴ | 0.04 | 0.54 |
| | | 9.25 × 10⁻⁴ | 9.72 | 8.29 |

TABLE XI

The following Table XI shows the results of anti-HIV-1 data on the oligopeptides of the present invention and their anti-HIV-1 activity is designated as inactive, moderate or active. Compounds 19b, 20b, 21b, 25b, 29, 30, 32, 34 and 36 are designated as active.

Anti-HIV-1 Activity

| Compound | IC$_{50}$ (µM) | EC$_{50}$ | TI$_{50}$ | Activity* |
|---|---|---|---|---|
| 3 | 83.5 | 11.9 | 7.01 | Moderate |
| 5 | 75.3 | 12 | 6.3 | Moderate |
| 8 | 64.8 | 5.3 | 12.1 | Moderate |
| 9 | — | — | — | Inactive |
| 10 | 51.1 | 2.1 | 24.1 | Moderate |
| 11 | — | — | — | Inactive |
| 12 | 57 | 3.9 | 1.46 | Moderate |
| 13 | 78 | 6.6 | 11.7 | Moderate |
| 15 | 41 | 41 | 1.0 | Inactive |
| 16 | >100 | — | — | Inactive |
| 17 | 29 | 14 | 2 | Moderate |
| 18 | >120 | — | — | Inactive |
| 19b | 17.9 | 1.21 | 14.8 | Active |
| 20b | 284 | 3.55 | 80 | Active |
| 21b | 33 | 1.37 | 24.1 | Active |
| 22b | 199 | 0.35 | 566 | Active |
| 23b | 9.3 | 3.44 | 2.7 | Moderate |
| 24b | 257 | 42.5 | 6.1 | Moderate |
| 25b | 68.2 | 0.42 | 161 | Active |
| 26b | 168 | 46.3 | 3.6 | Moderate |
| 27b | 181 | 5.6 | 32.4 | Moderate |
| 29 | 4.7 | 0.39 | 12 | Active |

TABLE XI-continued

The following Table XI shows the results of anti-HIV-1 data on the oligopeptides of the present invention and their anti-HIV-1 activity is designated as inactive, moderate or active. Compounds 19b, 20b, 21b, 25b, 29, 30, 32, 34 and 36 are designated as active.

Anti-HIV-1 Activity

| Compound | IC$_{50}$ (µM) | EC$_{50}$ | TI$_{50}$ | Activity* |
|---|---|---|---|---|
| 30 | 140 | 21 | 6.6 | Active |
| 32 | 69 | 1.6 | 43 | Active |
| 33 | 69 | 9.8 | 7.0 | Moderate |
| 34 | 140 | 13 | 11 | Active |
| 35 | 71 | 16 | 4.5 | Moderate |
| 36 | 207 | 10.4 | 19.8 | Active |
| 37 | 35 | — | — | Inactive |

*National Cancer Institute Designation

EXAMPLE 31

The following test was an evaluation of compounds according to the invention for inhibition of HBV DNA replication in cell culture.

DMVI ASSAY CONTROLS: Untreated Cells, 2',3'-ddC

Test compounds were in the form of powdered materials which were dissolved in DMSO at 30 mg/ml. Compounds were tested for antiviral activity at two concentrations, approximately 10-fold apart, starting in the range of 100 µg/ml (approximately 100 µM). Compounds were tested for toxicity starting at 300 µg/ml (some were tested starting at 100 µg/ml, and at 50 µg/ml and 10 µg/ml for antiviral activities; 2',3-ddC was requested as a positive control and was tested at the same concentrations.

Details of the assay methodology can be found in: Korba and Milman, 1991, Antiviral Res., 15:217. The antiviral evaluations were performed on two separate passages of cells. All wells, in all plates, were seeded at the same density and at the same time.

Due to inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are generally considered to be statistically significant (P<0.05) (Korba and Gerin, manuscript submitted for publication). The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 pg/µg cell DNA (average approximately 74 pg/µg cell DNA). In general, depressions in the levels of intracellular HBV DNA due to treatment with antiviral compounds are less pronounced, and occur more slowly, than depressions in the levels of HBV virion DNA (Korba and Milman, 1991, Antiviral Res., 15:217).

For reference, the manner in which the hybridization analyses were performed for these experiments results in an equivalence of approximately 1.0 pg intracellular HBV DNA/µg cellular DNA to 2–3 genomic copies per cell and 1.0 pg of extracellular HBV DNA/ml culture medium to 3×10$^5$ viral particles/ml.

Toxicity analyses were performed in order to assess whether any observed antiviral effects are due to a general effect on cell viability. The method used was uptake of neutral red dye, a standard and widely used assay for cell viability in a variety of virus-host systems, including HSV and HIV. Details of the procedure are provided in the toxicity table legends.

These studies were performed at the Division of Molecular Virology and Immunology (DMVI) of Georgetown University (GU) and were supported by contract between GU and the National Institute of Allergy and Infectious Diseases (NIAID) as part of the Hepatitis Antiviral Program of the NIAID.

TOXICITY EVALUATIONS (TABLE T1)

No significant toxicity (greater than 50% depression of the dye uptake levels observed in untreated cells) was observed for any of the test compounds at the concentrations used for the antiviral evaluations.

No significant toxicity (less than 50% of the dye uptake of untreated cells) was observed for any of the test compounds at the highest concentrations used in the toxicity evaluations. The toxicity of 2',3'-ddC was approximately the same as that previously observed in this culture system (Korba and Gerin, manuscript submitted for publication).

ANTIVIRAL EVALUATIONS (TABLES AV1 TO AV3)
CONTROLS

Within normal variations, levels of HBV virion DNA and intracellular HBV replication intermediates (HBV RI) remained constant in the untreated cells over the challenge period. The positive treatment control, 2,3'-dideoxycytosine(2',3'-ddC), induced significant depressions of HBV DNA replication at the concentration used (Table AV1). At 9 µM 2',3'-ddC, a 90% depression of HBV RI (relative to average levels in untreated cells) is typically observed in this assay system (Korba and Milman, 1991).

TEST COMPOUNDS

Compounds 2, 4–9 and 15 (see pages 68–70) exhibited no significant effect on HBV replication at the concentrations tested.

Compound 3 was a weak inhibitor of HBV replication. HBV virion DNA and HBV RI were depressed to a lesser degree than observed following treatment with 2', 3'-ddC.

Compounds 11 and 12 were moderate inhibitors of HBV replication. HBV virion DNA and HBV RI were depressed to a degree comparable to, but generally less than, that observed following treatment with 2',3'-ddC.

Compounds 14, 17 and 13 were potent inhibitors of HBV replication. HBV virion DNA and HBV RI were depressed to a degree comparable to, or greater than, that observed following treatment with 2',3'-ddC.

TABLE AV1

Effect of test compounds on HBV replication in 2.2.15 cell cultures

| WELL | TREATMENT | INTRA-CELLULAR HBV DNA* (pg/µg CELL DNA) | | HBV VIRION DNA$^\#$ (pg/ml CULTURE MEDIUM) | |
|---|---|---|---|---|---|
| | | MONO. | RI | DAY 0 | DAY 6 | DAY 9 |
| 114AA | UNTREATED CELLS | 2.5 | 78 | 57 | 61 | 59 |
| 114AB | UNTREATED CELLS | 2.2 | 81 | 49 | 62 | 62 |
| 114BA | UNTREATED CELLS | 2.1 | 70 | 55 | 87 | 92 |
| 114BB | UNTREATED CELLS | 2.5 | 67 | 57 | 70 | 72 |
| 114AC | 2',3'-ddC @ 50 µM | 1.2 | 2 | 57 | 26 | 0 |
| 114AD | 2',3'-ddC @ 50 µM | 1.4 | 2 | 51 | 28 | 0 |

TABLE AV1-continued

Effect of test compounds on HBV replication in 2.2.15 cell cultures

| WELL | TREATMENT | INTRA-CELLULAR HBV DNA* (pg/μg CELL DNA) | | HBV VIRION DNA# (pg/ml CULTURE MEDIUM) | | |
|---|---|---|---|---|---|---|
| | | MONO. | RI | DAY 0 | DAY 6 | DAY 9 |
| 114BC | 2',3'-ddC @ 50 μM | 1.8 | 1 | 58 | 30 | 0 |
| 114BD | 2',3'-ddC @ 50 μM | 1.7 | 1 | 59 | 20 | 0 |
| 114AG | 2',3'-ddC @ 10 μM | 2.5 | 9 | 63 | 43 | 7 |
| 114AH | 2',3'-ddC @ 10 μM | 2.5 | 7 | 66 | 47 | 5 |
| 114BG | 2',3'-ddC @ 10 μM | 2.0 | 8 | 78 | 54 | 6 |
| 114BH | 2',3'-ddC @ 10 μM | 2.0 | 5 | 68 | 45 | 8 |
| 114AQ | Compound 9 @ 50 μM | 2.7 | 70 | 58 | 64 | 62 |
| 114AR | Compound 9 @ 50 μM | 2.9 | 86 | 69 | 74 | 65 |
| 114BQ | Compound 9 @ 50 μM | 2.8 | 66 | 77 | 50 | 71 |
| 114BR | Compound 9 @ 50 μM | 2.2 | 90 | 68 | 51 | 80 |
| 114AS | Compound 9 @ 10 μM | 2.3 | 77 | 68 | 71 | 63 |
| 114AT | Compound 9 @ 10 μM | 2.6 | 80 | 97 | 85 | 81 |
| 114BS | Compound 9 @ 10 μM | 2.7 | 60 | 60 | 52 | 74 |
| 114BT | Compound 9 @ 10 μM | 2.7 | 65 | 80 | 72 | 79 |
| 114AU | Compound 7 @ 50 μM | 2.7 | 54 | 96 | 67 | 63 |
| 114AV | Compound 7 @ 50 μM | 2.5 | 55 | 72 | 75 | 68 |
| 114BU | Compound 7 @ 50 μM | 2.3 | 64 | 81 | 83 | 77 |
| 114BV | Compound 7 @ 50 μM | 2.3 | 63 | 44 | 69 | 66 |
| 114AW | Compound 7 @ 10 μM | 2.1 | 81 | 75 | 68 | 56 |
| 114AX | Compound 7 @ 10 μM | 2.3 | 87 | 92 | 67 | 57 |
| 114BW | Compound 7 @ 10 μM | 2.2 | 68 | 60 | 57 | 87 |
| 114BX | Compound 7 @ 10 μM | 2.6 | 65 | 55 | 50 | 58 |

*Analysis of intracellular HBV DNA was 24 hours following the 9th day of treatment. DNA in each cell DNA preparation were used to calculate the levels of episomal 3.2 Kb HBV genomes (MONO.) and HBV DNA replication intermediates (RI).
A "zero" indicates an undetectable level of HBV DNA, sensitivity cutoff was 0.1 pg/ml.

TABLE AV2

Effect of test compounds on HBV replication in 2.2.15 cell cultures

| WELL | TREATMENT | INTRA-CELLULAR HBV DNA* (pg/μg CELL DNA) | | HBV VIRION DNA# (pg/ml CULTURE MEDIUM) | | |
|---|---|---|---|---|---|---|
| | | MONO. | RI | DAY 0 | DAY 6 | DAY 9 |
| 115AA | Compound 2 @ 50 μM | 1.3 | 55 | 74 | 68 | 62 |
| 115AB | Compound 2 @ 50 μM | 2.3 | 64 | 93 | 62 | 74 |
| 115BA | Compound 2 @ 50 μM | 2.4 | 67 | 77 | 73 | 80 |
| 115BB | Compound 2 @ 50 μM | 2.4 | 73 | 61 | 83 | 99 |
| 115AC | Compound 2 @ 10 μM | 1.9 | 84 | 77 | 62 | 100 |
| 115AD | Compound 2 @ 10 μM | 2.3 | 98 | 91 | 68 | 86 |
| 115BC | Compound 2 @ 10 μM | 2.3 | 73 | 62 | 61 | 77 |
| 115BD | Compound 2 @ 10 μM | 2.2 | 91 | 66 | 74 | 56 |
| 115AE | Compound 4 @ 50 μM | 2.5 | 94 | 63 | 86 | 97 |
| 115AF | Compound 4 @ 50 μM | 2.8 | 76 | 66 | 70 | 65 |
| 115BE | Compound 4 @ 50 μM | 2.1 | 74 | 78 | 64 | 61 |
| 115BF | Compound 4 @ 50 μM | 2.4 | 73 | 74 | 88 | 85 |
| 115AG | Compound 4 @ 10 μM | 2.3 | 85 | 77 | 52 | 73 |
| 115AH | Compound 4 @ 10 μM | 2.8 | 91 | 61 | 55 | 81 |
| 115BG | Compound 4 @ 10 μM | 2.3 | 54 | 77 | 96 | 62 |
| 115BH | Compound 4 @ 10 μM | 2.1 | 6.2 | 64 | 59 | 50 |
| 115AI | Compound 5 @ 50 μM | 1.8 | 51 | 58 | 82 | 44 |
| 115AJ | Compound 5 @ 50 μM | 2.8 | 53 | 56 | 74 | 59 |
| 115BI | Compound 5 @ 50 μM | 2.2 | 60 | 66 | 90 | 61 |
| 115BJ | Compound 5 @ 50 μM | 2.1 | 70 | 55 | 54 | 78 |
| 115AK | Compound 5 @ 10 μM | 2.3 | 98 | 56 | 94 | 62 |
| 115AL | Compound 5 @ 10 μM | 2.5 | 70 | 87 | 83 | 80 |
| 115BK | Compound 5 @ 10 μM | 2.9 | 88 | 68 | 60 | 90 |
| 115BL | Compound 5 @ 10 μM | 2.9 | 69 | 50 | 81 | 89 |
| 115AM | Compound 6 @ 50 μM | 1.5 | 66 | 71 | 62 | 95 |
| 115AN | Compound 6 @ 50 μM | 1.6 | 60 | 72 | 75 | 75 |
| 115BM | Compound 6 @ 50 μM | 2.6 | 77 | 72 | 55 | 64 |
| 115BN | Compound 6 @ 50 μM | 2.3 | 80 | 88 | 57 | 91 |
| 115AO | Compound 6 @ 10 μM | 1.6 | 68 | 56 | 87 | 80 |
| 115AP | Compound 6 @ 10 μM | 2.8 | 51 | 71 | 61 | 81 |
| 115BO | Compound 6 @ 10 μM | 2.2 | 50 | 86 | 64 | 97 |
| 115BP | Compound 6 @ 10 μM | 2.0 | 57 | 96 | 68 | 69 |
| 115AQ | Compound 3 @ 50 μM | 2.9 | 27 | 58 | 67 | 16 |
| 115AR | Compound 3 @ 50 μM | 2.2 | 23 | 58 | 44 | 13 |
| 115BQ | Compound 3 @ 50 μM | 2.2 | 26 | 68 | 78 | 19 |
| 115BR | Compound 3 @ 50 μM | 2.4 | 25 | 81 | 76 | 10 |

TABLE AV2-continued

Effect of test compounds on HBV replication in 2.2.15 cell cultures

| WELL | TREATMENT | INTRACELLULAR HBV DNA* (pg/μg CELL DNA) | | HBV VIRION DNA# (pg/ml CULTURE MEDIUM) | | |
|---|---|---|---|---|---|---|
| | | MONO. | RI | DAY 0 | DAY 6 | DAY 9 |
| 115AS | Compound 3 @ 50 μM | 2.8 | 97 | 57 | 79 | 69 |
| 115AT | Compound 3 @ 10 μM | 2.2 | 86 | 64 | 83 | 74 |
| 115BS | Compound 3 @ 10 μM | 2.6 | 81 | 74 | 38 | 94 |
| 115BT | Compound 3 @ 10 μM | 2.5 | 62 | 60 | 97 | 92 |
| 115AU | Compound 8 @ 50 μM | 2.2 | 75 | 55 | 50 | 55 |
| 115AV | Compound 8 @ 50 μM | 2.6 | 55 | 77 | 38 | 54 |
| 115BU | Compound 8 @ 50 μM | 2.5 | 77 | 58 | 48 | 70 |
| 115BV | Compound 8 @ 50 μM | 2.8 | 80 | 79 | 44 | 75 |
| 115AW | Compound 8 @ 10 μM | 2.9 | 58 | 81 | 78 | 59 |
| 115AX | Compound 8 @ 10 μM | 2.5 | 65 | 63 | 58 | 58 |
| 115BW | Compound 8 @ 10 μM | 2.1 | 50 | 62 | 58 | 82 |
| 115BX | Compound 8 @ 10 μM | 2.2 | 66 | 82 | 80 | 87 |

*Analysis of intracellular HBV DNA was 24 hours following the 9th day of treatment. DNA in each cell DNA preparation were used to calculate the levels of episomal 3.2 Kb HBV genomes (MONO.) and HBV DNA replication intermediates (RI).
A "zero" indicates an undetectable level of HBV DNA, sensitivity cutoff was 0.1 pg/ml.

TABLE AV3

Effect of test compounds on HBV replication in 2.2.15 cell cultures

| WELL | TREATMENT | INTRACELLULAR HBV DNA* (pg/μg CELL DNA) | | HBV VIRION DNA# (pg/ml CULTURE MEDIUM) | | |
|---|---|---|---|---|---|---|
| | | MONO. | RI | DAY 0 | DAY 6 | DAY 9 |
| 116AA | Compound 11 @ 50 μM | 2.4 | 8 | 78 | 38 | 2 |
| 116AB | Compound 11 @ 50 μM | 2.5 | 7 | 69 | 24 | 2 |
| 116BA | Compound 11 @ 50 μM | 2.3 | 7 | 89 | 48 | 4 |
| 116BB | Compound 11 @ 50 μM | 2.4 | 9 | 95 | 45 | 3 |
| 116AC | Compound 11 @ 10 μM | 2.0 | 58 | 87 | 77 | 30 |
| 116AD | Compound 11 @ 10 μM | 1.9 | 85 | 85 | 98 | 22 |
| 116BC | Compound 11 @ 10 μM | 2.2 | 83 | 79 | 74 | 20 |
| 116BD | Compound 11 @ 10 μM | 2.3 | 61 | 55 | 82 | 25 |
| 116AE | Compound 15 @ 50 μM | 2.2 | 64 | 55 | 68 | 54 |
| 116AF | Compound 15 @ 50 μM | 2.1 | 74 | 54 | 70 | 66 |
| 116BE | Compound 15 @ 50 μM | 2.4 | 67 | 57 | 52 | 44 |
| 116BF | Compound 15 @ 50 μM | 2.5 | 83 | 75 | 98 | 65 |
| 116AG | Compound 15 @ 10 μM | 2.3 | 62 | 98 | 42 | 59 |
| 116AH | Compound 15 @ 10 μM | 2.3 | 58 | 51 | 62 | 70 |
| 116BG | Compound 15 @ 10 μM | 2.2 | 84 | 87 | 52 | 94 |
| 116BH | Compound 15 @ 10 μM | 2.5 | 82 | 78 | 60 | 54 |
| 116AI | Compound 12 @ 50 μM | 1.8 | 11 | 59 | 21 | 9 |
| 116AJ | Compound 12 @ 50 μM | 1.0 | 10 | 50 | 19 | 8 |
| 116BI | Compound 12 @ 50 μM | 1.2 | 9 | 99 | 31 | 11 |
| 116BJ | Compound 12 @ 50 μM | 1.1 | 12 | 52 | 29 | 14 |
| 116AK | Compound 12 @ 10 μM | 2.0 | 57 | 42 | 97 | 55 |
| 116AL | Compound 12 @ 10 μM | 2.0 | 68 | 48 | 98 | 91 |
| 116BK | Compound 12 @ 10 μM | 1.9 | 58 | 52 | 79 | 54 |
| 116BL | Compound 12 @ 10 μM | 1.9 | 79 | 84 | 81 | 81 |
| 116AM | Compound 14 @ 50 μM | 1.9 | 6 | 71 | 26 | 1 |
| 116AN | Compound 14 @ 50 μM | 2.0 | 2 | 89 | 27 | 1 |
| 116BM | Compound 14 @ 50 μM | 2.3 | 3 | 51 | 36 | 1 |
| 116BN | Compound 14 @ 50 μM | 2.0 | 8 | 92 | 37 | 1 |
| 116AO | Compound 14 @ 10 μM | 2.5 | 70 | 50 | 110 | 21 |
| 116AP | Compound 14 @ 10 μM | 2.2 | 54 | 61 | 120 | 25 |
| 116BO | Compound 14 @ 10 μM | 2.3 | 80 | 55 | 77 | 22 |
| 116BP | Compound 14 @ 10 μM | 2.1 | 75 | 67 | 87 | 20 |
| 116AQ | Compound 17 @ 50 μM | 2.4 | 4 | 63 | 73 | 4 |
| 116AR | Compound 17 @ 50 μM | 2.7 | 8 | 56 | 68 | 2 |
| 116BQ | Compound 17 @ 50 μM | 2.3 | 7 | 66 | 63 | 3 |
| 116BR | Compound 17 @ 50 μM | 2.4 | 5 | 60 | 89 | 3 |
| 116AS | Compound 17 @ 10 μM | 2.6 | 43 | 46 | 130 | 55 |
| 116AT | Compound 17 @ 10 μM | 2.5 | 51 | 45 | 140 | 84 |
| 116BS | Compound 17 @ 10 μM | 2.1 | 68 | 63 | 65 | 50 |
| 116BT | Compound 17 @ 10 μM | 2.2 | 62 | 52 | 73 | 84 |
| 116AU | Compound 13 @ 50 μM | 2.5 | 5 | 50 | 47 | 7 |
| 116AV | Compound 13 @ 50 μM | 1.8 | 5 | 48 | 52 | 8 |
| 116BU | Compound 13 @ 50 μM | 2.0 | 6 | 99 | 78 | 6 |
| 116BV | Compound 13 @ 50 μM | 2.3 | 7 | 88 | 50 | 5 |
| 116AW | Compound 13 @ 10 μM | 2.2 | 77 | 59 | 130 | 100 |

TABLE AV3-continued

Effect of test compounds on HBV replication in 2.2.15 cell cultures

| | | INTRA-CELLULAR HBV DNA* (pg/μg CELL DNA) | | HBV VIRION DNA# (pg/ml CULTURE MEDIUM) | | |
|---|---|---|---|---|---|---|
| WELL | TREATMENT | MONO. | RI | DAY 0 | DAY 6 | DAY 9 |
| 116AX | Compound 13 @ 10 μM | 2.1 | 78 | 60 | 110 | 54 |
| 116BW | Compound 13 @ 10 μM | 2.6 | 90 | 94 | 88 | 47 |
| 116BX | Compound 13 @ 10 μM | 2.4 | 61 | 67 | 69 | 80 |

*Analysis of intracellular HBV DNA was 24 hours following the 9th day of treatment. DNA in each cell DNA preparation were used to calculate the levels of episomal 3.2 Kb HBV genomes (MONO.) and HBV DNA replication intermediates (RI).
A "zero" indicates an undetectable level of HBV DNA, sensitivity cutoff was 0.1 pg/ml.

TABLE T1

Toxicity analysis of test compounds in 2.2.15 cell

| | | NEUTRAL RED DYE UPTAKE AT INDICATED DRUG CONCENTRATION (% OF CONTROL) | | | |
|---|---|---|---|---|---|
| PLATE | COMPOUND | 300 μg/ml | 100 μg/ml | 30 μg/ml | 10 μg/ml |
| 27 | 2',3'-ddC | 17 ± 2 | 89 ± 3 | 100 ± 1 | 99 ± 1 |
| 25 | Compound 9 | 99 ± 1 | 100 ± 2 | 99 ± 1 | 102 ± 3 |
| 25 | Compound 7 | 98 ± 2 | 101 ± 2 | 102 ± 1 | 101 ± 2 |
| 25 | Compound 4 | 99 ± 1 | 100 ± 1 | 101 ± 1 | 99 ± 1 |
| 26 | Compound 3 | 82 ± 2 | 99 ± 2 | 99 ± 1 | 99 ± 1 |
| 26 | Compound 8 | 84 ± 1 | 99 ± 2 | 99 ± 2 | 100 ± 1 |
| 26 | Compound 11 | 84 ± 2 | 100 ± 1 | 101 ± 2 | 99 ± 2 |
| 26 | Compound 15 | 76 ± 2 | 101 ± 1 | 101 ± 2 | 99 ± 3 |
| 26 | Compound 12 | 82 ± 4 | 101 ± 1 | 99 ± 1 | 101 ± 1 |
| 26 | Compound 14 | 85 ± 2 | 99 ± 1 | 98 ± 1 | 99 ± 2 |
| 27 | Compound 17 | 82 ± 1 | 99 ± 1 | 100 ± 1 | 100 ± 2 |
| 27 | Compound 13 | 79 ± 1 | 98 ± 1 | 99 ± 2 | 99 ± 1 |

| | | NEUTRAL RED DYE UPTAKE AT INDICATED DRUG CONCENTRATION (% OF CONTROL) | | | |
|---|---|---|---|---|---|
| PLATE | COMPOUND | 100 μg/ml | 30 μg/ml | 10 μg/ml | 3 μg/ml |
| 25 | Compound 2 | 96 ± 1 | 100 ± 1 | 101 ± 2 | 102 ± 1 |
| 25 | Compound 5 | 101 ± 2 | 100 ± 1 | 99 ± 2 | 101 ± 1 |
| 26 | Compound 6 | 85 ± 4 | 101 ± 1 | 98 ± 1 | 100 ± 2 |

Toxicity analyses were performed in 96-well flat bottomed tissue culture plates. Cells for the toxicity analyses were cultured and treated with test compounds with the same schedule as used for the antiviral evaluations. Each compound was tested at 4 concentrations, each in triplicate cultures. Uptake of neutral red dye was used to determine the relative level of toxicity. The absorbance of internalized dye at 510 nM ($A_{510}$) was used for the quantitative analysis. Values are presented as a percentage of the average $A_{510}$ values (±standard deviations) in 9 separate cultures of untreated cells maintained on the same 96-well plate as the test compounds. The percentage of dye uptake in the 9 control cultures on plate 25 was 100±1, on plate 26, 100±2, and on plate 27, 100±2.

Bis-lexitropsins: Lex–C(=O)–L–C(=O)–Lex

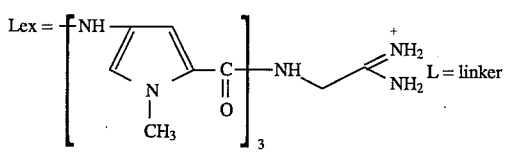

L = linker

| L | MF and MW | Amount (mg) | Solubility in | | |
|---|---|---|---|---|---|
| | | | DMSO | MeOH | H$_2$O |
| 1  | C$_{50}$H$_{58}$N$_{18}$O$_8$Cl$_2$ 1108 | 3.6 | good | partial | fair |
| 2  | C$_{50}$H$_{58}$N$_{18}$O$_8$Cl$_2$ 1108 | 4.6 | good | good | good |

-continued

Bis-lexitropsins: Lex-C(=O)-L-C(=O)-Lex

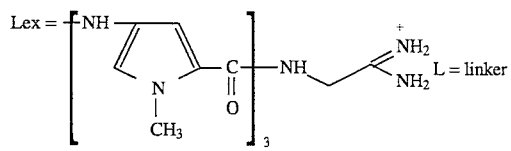

Lex = -[NH-(pyrrole with N-CH₃)-C(=O)-NH-CH₂-C(NH₂)=NH₂⁺]₃, L = linker

| L | | MF and MW | Amount (mg) | Solubility in DMSO | MeOH | H₂O |
|---|---|---|---|---|---|---|
| 3 | o-xylyl | $C_{50}H_{58}N_{18}O_8Cl_2$ 1108 | 3.3 | good | good | good |
| 4 | 2,6-pyridyl | $C_{49}H_{57}N_{19}O_8Cl_2$ 1109 | 3.0 | good | good | good |
| 5 | 3,5-pyridyl | $C_{49}H_{57}N_{19}O_8Cl_2$ 1109 | 3.7 | good | good | good |
| 6 | 2,5-pyridyl | $C_{49}H_{57}N_{19}O_8Cl_2$ 1109 | 3.7 | good | fair | good |
| 7 | cyclobutyl | $C_{48}H_{60}N_{18}O_8Cl_2$ 1086 | 3.7 | good | good | good |
| 8 | bicyclic | $C_{51}H_{62}N_{18}O_8Cl_2$ 1175 | 4.5 | good | good | good |
| 9 | trans-CH=CH | $C_{46}H_{56}N_{18}O_8Cl_2$ 1058 | 3.8 | good | good | good |
| 10 | cis-CH=CH | $C_{46}H_{56}N_{18}O_8Cl_2$ 1058 | 1.5 | good | good | good |
| 11 | 1,3,5-benzenetriyl | $C_{72}H_{84}N_{27}O_{12}Cl_3$ 1624.5 | 4.2 | good | good | good |
| 12 | —(CH₂)₂— | $C_{46}H_{112}N_{18}O_8Cl_2$ 1115 | 4.1 | good | good | good |
| 13 | —(CH₂)₆— | $C_{50}H_{120}N_{18}O_8Cl_2$ 1171 | 4.8 | good | good | good |
| 14 | —(CH₂)₈— | $C_{52}H_{124}N_{18}O_8Cl_2$ 1199 | 4.2 | good | good | good |
| 15 | —(CH₂)₂₂— | $C_{66}H_{152}N_{18}O_8Cl_2$ 1395 | 4.3 | good | poor | partial |
| 16* | Im-C(=O)-CH=CH-C(=O)-Im | $C_{34}H_{50}N_{16}O_6Cl_2$ 849 | 3.0 | fair | poor | good |

Bis-lexitropsins: Lex-C(=O)-L-C(=O)-Lex

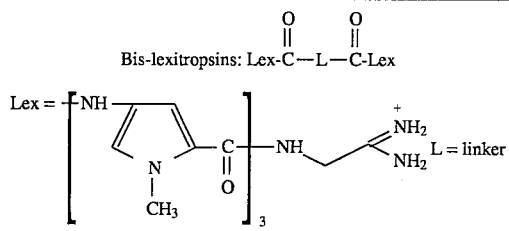

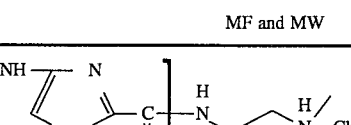

| L | MF and MW | Amount (mg) | Solubility in DMSO | MeOH | H$_2$O |
|---|---|---|---|---|---|
| 17 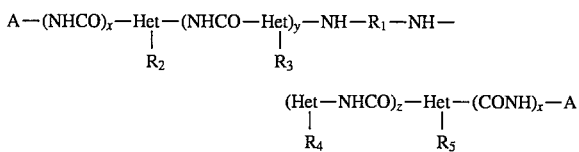 | | | Similar to Compound 1 but prepared by different procedure and with different water of crystallization | | |

RESULTS

A wide range of activities was found among the compounds which were tested. All were tested at 50 and 10 μm. The most potent compounds (Compounds 11, 12, 14, 17 and 13) had activities just slightly less than that observed with the control (2', 3'-ddC). All exhibited very little toxicity in the confluent cells used for both the antiviral screening and toxicity testing.

We claim:

1. A method for treating a patient infected with Human Immunodeficiency Virus, comprising administering to the patient an anti-HIV effective amount of a compound of the formula:

$$A-(NHCO)_x-\underset{R_2}{Het}-(NHCO-Het)_y-NH-R_1-NH-$$
$$(Het-NHCO)_z-\underset{R_4}{Het}-(CONH)_x-A$$
(with $R_3$ on the first Het line and $R_5$ on the second Het line)

wherein:

A is a moiety bearing a positive charge and of a size which does not inhibit binding of said compound to nucleic acid sequences associated with the cellular action of Human Immunodeficiency Viruses;

$R_1$ is a moiety derived from a residue of carbonic acid or a residue of a dicarboxylic acid selected from the group consisting of:
(i) a residue of a dicarboxylic acid of the formula —CO—$C_p$—H$_{2p}$—CO where p equals 1 to 22;
(ii) a residue of an unsaturated aliphatic dicarboxylic acid of the formula —CO—$C_q$—H$_{2q-2}$—CO— where q equals 2 to 22;
(iii) a residue of an aromatic dicarboxylic acid;
(iv) a residue of a cycloalkane dicarboxylic acid of the formula —CO—$C_r$—H$_{2r-2}$—CO— where r equals 3 to 7, optionally fused to one or more three to seven membered C rings; and
(v) a residue of a cycloalkene dicarboxylic acid of the formula —CO—$C_s$—H$_{2s-4}$—CO where s equals 3 to 7;

Hew is pyrrole;

x is 0 or 1;

y is 0, 1, 2 or 3;

z is 0, 1, 2 or 3;

$R_2$, $R_3$, $R_4$ and $R_5$ are attached to a ring atom other than carbon and are independently selected from the group consisting of $C_1$–$C_6$ alkyl and —CH$_2$—O—$R_6$, where $R_6$ is a $C_1$–$C_6$ alkyl;

and salts thereof.

2. The method of claim 1, wherein A is a moiety selected from the group consisting of an amidine, a guanidine, secondary ammonium salts, tertiary ammonium salts, quaternary ammonium salts, sulfonium salts and phosphonium salts.

3. The method of claim 1, wherein $R_2$, $R_3$, $R_4$ and $R_5$ are each a $C_1$–$C_6$ alkyl.

4. The method of claim 1, wherein $R_2$, $R_3$, $R_4$ and $R_5$ are the same and are a $C_1$–$C_6$ alkyl group.

5. The method of claim 1, wherein $R_2$, $R_3$, $R_4$ and $R_5$ are each a methoxymethyl.

6. The method of claim 1, wherein $R_1$ is

7. The method of claim 1, wherein $R_1$ is a residue of a dicarboxylic acid of the formula —CO—$C_p$H$_{2p}$—CO— where p equals 1 to 22.

8. The method of claim 1, wherein $R_1$ is a residue of a dicarboxylic acid selected from the group consisting of: a residue of an unsaturated aliphatic dicarboxylic acid of the formula —CO—$C_q$—H$_{2q-2}$—CO— where q equals 2; a residue of an aromatic dicarboxylic acid; and a residue of a cycloalkane dicarboxylic acid of the formula —CO—$C_r$—H$_{2r-2}$—CO— where r equals 3 to 6.

9. The method of claim 1, wherein the compound is N,N'-di[1-methyl-2-[1-methyl-2-carboximido(3-propionamidine)-4-pyrrole]-4-pyrrolyl] terephthalamide dihydrochloride.

10. The method of claim 1, wherein the compound is N,N'-di[1-methyl-2-[1-methyl-2-carboximido(3-propionamidine)-4-pyrrole]-4-pyrrolyl] isophthalamide dihydrochloride.

11. The method of claim 1, wherein the compound is N,N'-di[1-methyl-2-[1-methyl-2-carboximido(3-propionamidine)-4-pyrrole]-4-pyrrolyl] fumaramide dihydrochloride.

12. The method of claim 1, wherein the compound is N,N'-di[1-methyl-2-[1-methyl-2-carboximido(3-propionamidine)-4-pyrrole]-4-pyrrolyl] maleamide dihydrochloride.

13. The method of claim 1, wherein the compound is N,N'-di[1-methyl-2-[1-methyl-2-carboximido(3-propionamidine)-4-pyrrole]-4-pyrrolyl] trans 1,2-cyclobutanamide dihydrochloride.

14. The method of claim 1, wherein the compound is:

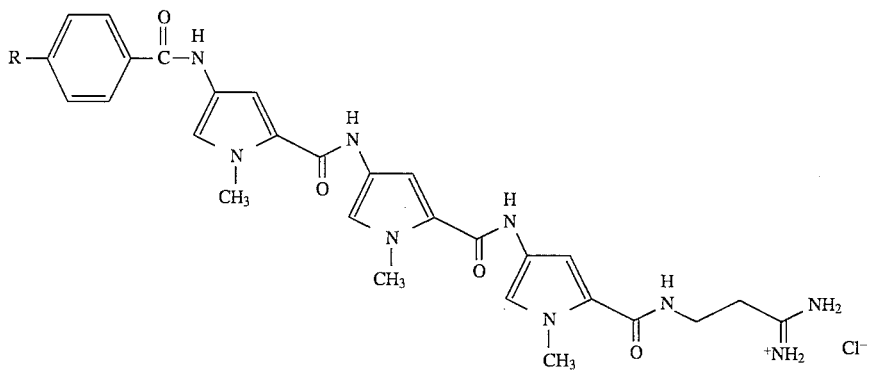

and R is

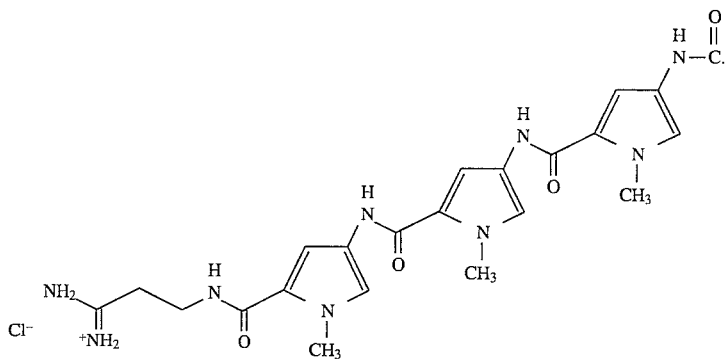

15. The method of claim 1, wherein the compound is:

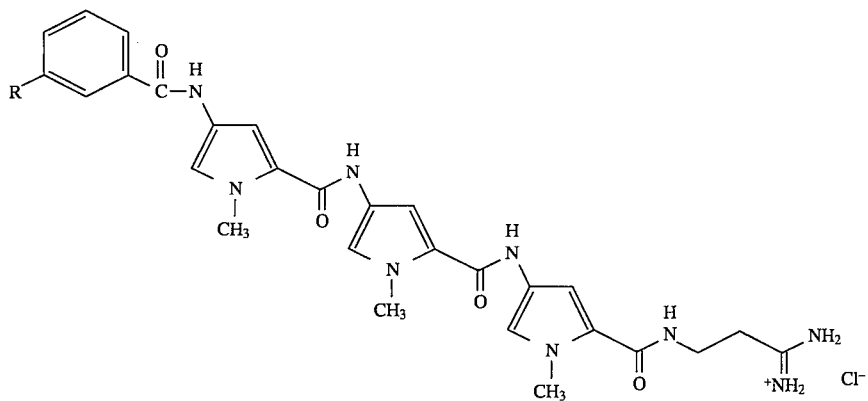
and R is
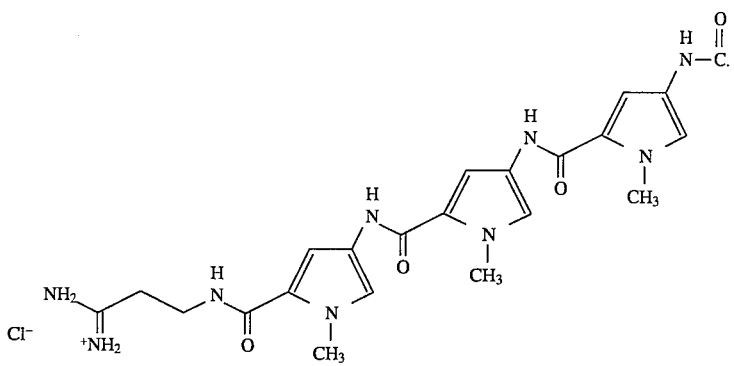
16. The method of claim 1, wherein the compound is:
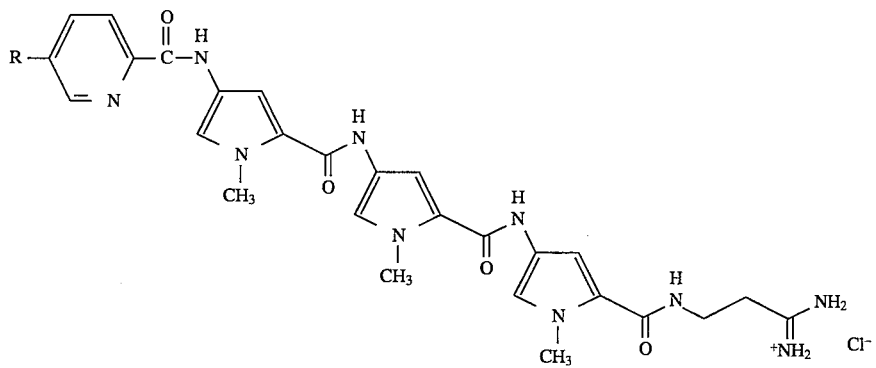
and R is

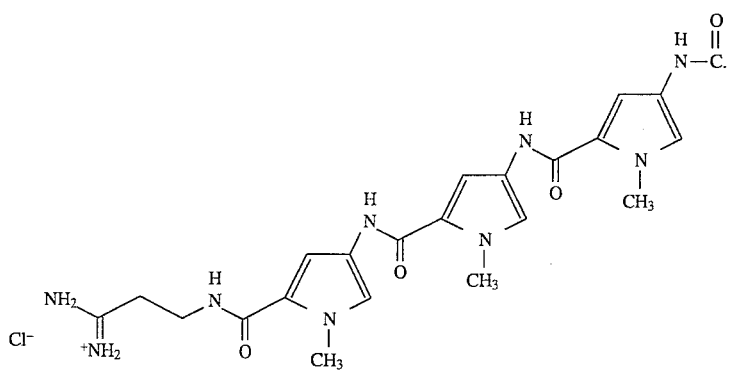
17. The method of claim 1, wherein the compound is: and R is
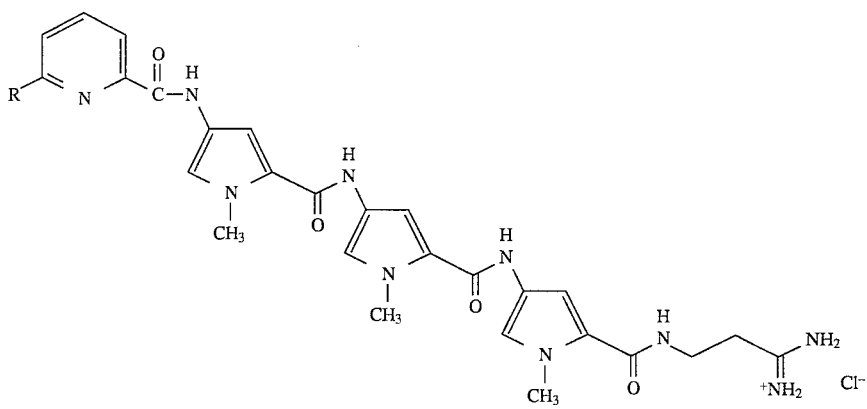
and R is
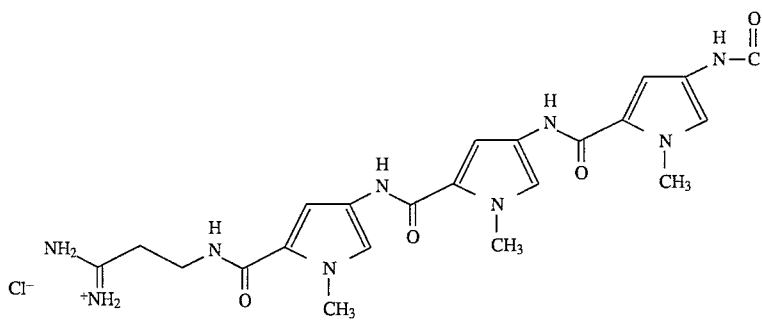
18. The method of claim 1, wherein the compound is:
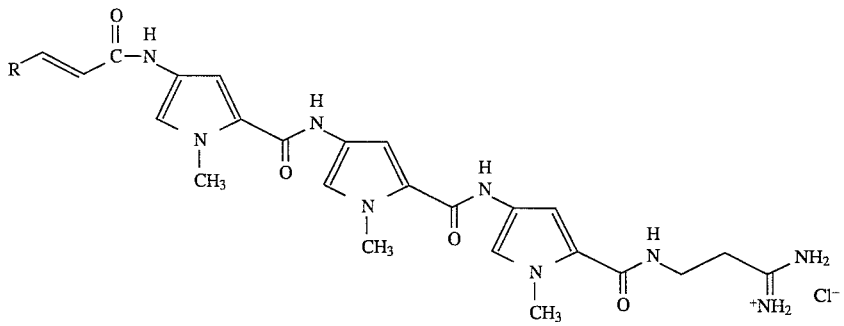

19. The method of claim 1, wherein the anti-HIV effective dose is in a range of 1 to 200 mg/kg body weight per day.

20. The method of claim 1, wherein the compound is administered intraveneously or orally.

21. A compound exhibiting activity against Human Immunodeficiency Virus, represented by the formula:

$$A-(NHCO)_x-\underset{R_2}{Het}-(NHCO-\underset{R_3}{Het})_y-NH-R_1-NH-$$
$$-(\underset{R_4}{Het}-NHCO)_z-\underset{R_5}{Het}-(CONH)_x-A$$

wherein $R_1$ is a moiety derived from a residue of a dicarboxylic acid selected from the group consisting of: a residue of a $C_6$ aromatic dicarboxylic acid; a residue of an unsaturated aliphatic dicarboxylic acid of the formula $CO-C_q-H_{2q-2}-CO-$ where q equals 2; a residue of a cycloalkane dicarboxylic acid of the formula $CO-C_r-H_{2r-2}-CO$ where r equals 3 to 6 optionally fused to one or more three to seven C membered rings, and A, x, y and z are as defined in claim 1 and $R_2$, $R_3$, $R_4$, and $R_5$ are attached to a ring atom other than carbon and are independently selected from the group consisting of $C_2$-$C_6$ alkyl and $-CH_2-O-R_6$ where $R_6$ is a $C_1$-$C_6$ alkyl; and salts thereof.

22. The compound of claim 21, wherein $R_1$ is

[structures: para-phenylene dicarbonyl or meta-phenylene dicarbonyl]

23. The compound of claim 21, wherein $R_1$ is

[structure with CO or CO / CO / CO]

24. The compound of claim 21, wherein $R_1$ is a dicarboxylic acid residue of cyclopropane.

25. The compound of claim 21, wherein $R_1$ is a dicarboxylic acid residue of cyclopentane.

26. The compound of claim 21, wherein $R_1$ is a dicarboxylic acid residue of cyclohexane.

27. The compound of claim 21, wherein $R_1$ is

[pyridine-2,5-dicarbonyl structure]

28. The compound of claim 21, wherein $R_1$ is

[pyridine-2,6-dicarbonyl structure]

29. A pharmaceutical composition suitable for the treatment of Human Immunodeficiency Virus infections, comprising a compound of the formula:

$$A-(NHCO)_x-\underset{R_2}{Het}-(NHCO-\underset{R_3}{Het})_y-NH-R_1-NH-(\underset{R_4}{Het}-NHCO)_z-\underset{R_5}{Het}-(CONH)_x-A$$

wherein:

A is a moiety bearing a positive charge and of a size which does not inhibit binding of said compound to nucleic acid sequences associated with the cellular action of retroviruses;

$R_1$ is a moiety derived from a residue of carbonic acid or a residue of a dicarboxylic acid selected from the group consisting of:
  (i) a residue of a dicarboxylic acid of the formula $-CO-C_p-H_{2p}-CO$ where p equals 1 to 16;
  (ii) a residue of an unsaturated aliphatic dicarboxylic acid of the formula $-CO-C_q-H_{2q-2}-CO-$ where q equals 2 to 16;
  (iii) a residue of an aromatic dicarboxylic acid;
  (iv) a residue of a cycloalkane dicarboxylic acid of the formula $-CO-C_r-H_{2r-2}-CO-$ where r equals 3 to 7 optionally fused to one or more three to six C membered rings; and
  (v) a residue of a cycloalkene dicarboxylic acid of the formula $-CO-C_s-H_{2s-4}-CO$ where s equals 3 to 7;

Hew is pyrrole;

X is 0 or 1;

y is 0, 1, 2 or 3;

z is 0, 1, 2 or 3;

$R_2$, $R_3$, $R_4$ and $R_5$ are attached to a ring atom other than carbon and are independently selected from the group consisting of $C_2$-$C_6$ alkyl and —$CH_2$—O—$R_6$ is a $C_1$-$C_6$ alkyl; and salts thereof, in a pharmaceutically acceptable carrier.

30. A process for the preparation of a compound of the formula:

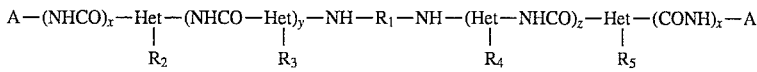

wherein:

A is a moiety bearing a positive charge and of a size which does not inhibit binding of said compound to nucleic acid sequences associated with the cellular action of retroviruses;

$R_1$ is a moiety derived from a residue of carbonic acid or a residue of a dicarboxylic acid selected from the group consisting of:

(i) a residue of a dicarboxylic acid of the formula —CO—$C_p$—$H_{2p}$—CO where p equals 1 to 16;

(ii) a residue of an unsaturated aliphatic dicarboxylic acid of the formula —CO—$C_q$—$H_{2q-2}$—CO— where q equals 2 to 16;

(iii) a residue of an aromatic dicarboxylic acid;

(iv) a residue of a cycloalkane dicarboxylic acid of the formula —CO—$C_r$—$H_{2r-2}$—CO— where r equals 3 to 7 optionally fused to a three to seven C membered ring; and (v) a residue of a cycloalkene dicarboxylic acid of the formula —CO—$C_s$—$H_{2s-4}$—CO where s equals 3 to 7;

Hew is a five membered heterocyclic moiety selected from the group consisting of a pyrrole, an imidazole, a triazole, a pyrazole, a thiazole, a thiophene, a furan and an oxazole;

x is 0 or 1;

y is 0, 1, 2 or 3;

z is 0, 1, 2 or 3;

$R_2$, $R_3$, $R_4$ and $R_5$ are attached to a ring atom other than carbon and are independently selected from the group consisting of $C_2$-$C_6$ alkyl and —$CH_2$—O—$R_6$ where $R_6$ is a $C_1$-$C_6$ alkyl;

and salts thereof, comprising the steps of:

reacting a compound of the formula (II)

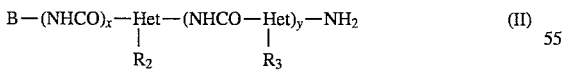

with a dicarboxylic acid of the formula (III)

$$X—R_1—X \qquad (III)$$

and converting B to A to form said moiety bearing a positive charge, wherein;

x, y and $R_1$ are as defined above;

B is the same as A or is a group with a nitrile, halogen or sulfide substituent; and X is a halogen, imidazolide or other reactive moiety.

31. A method for treating a patient infected with Hepatitis B, comprising administering to the patient an antiretroviral effective amount of a compound of the formula:

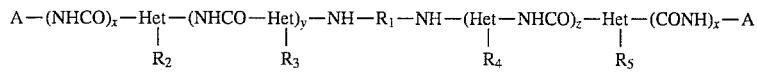

wherein:

A is a moiety bearing a positive charge and a size which does not inhibit binding of said compound to nucleic acid sequences associated with the cellular action of Hepatitis B;

$R_1$ is a moiety derived from a residue of carbonic acid or a residue of a dicarboxylic acid selected from the group consisting of:

(i) a residue of a dicarboxylic acid of the formula —CO—$C_p$—$H_{2p}$—CO where p equals 1 to 22;

(ii) a residue of an unsaturated aliphatic dicarboxylic acid of the formula —CO—$C_q$—$H_{2q-2}$—CO— where q equals 2 to 22;

(iii) a residue of an aromatic dicarboxylic acid;

(iv) a residue of a cycloalkane dicarboxylic acid of the formula —CO—$C_r$—$H_{2r-2}$—CO— wherein r equals 3 to 7, optionally fused to one or more three to seven membered C rings; and (v) a residue of a cycloalkene dicarboxylic acid of the formula —CO—$C_s$—$H_{2s-4}$—CO— where s equals 3 to 7;

Hew is a five membered heterocyclic moiety selected from the group consisting of a pyrrole, an imidazole, a triazole, a pyrazole, a thiazole, a thiophene, a furan and an oxazole;

x is 0 or 1;

y is 0, 1, 2 or 3;

z is 0, 1, 2 or 3;

$R_2$, $R_3$, $R_4$ and $R_5$ are attached to a ring atom other than carbon and are independently selected from the group consisting of $C_1$-$C_6$ alkyl and —$CH_2$—O—$R_6$, where $R_6$ is a $C_1$-$C_6$ alkyl;

or a salt thereof.

* * * * *